United States Patent [19]

Vermeulen et al.

[11] Patent Number: 5,789,233
[45] Date of Patent: Aug. 4, 1998

[54] DNA ENCODING AN EIMEKIA 50 KD ANTIGEN

[75] Inventors: Arnoldus Nicolaas Vermeulen, Cuijk; Paul van den Boogaart, Oss; Jacobus Johannus Kok, Nijmegen, all of Netherlands

[73] Assignee: Akzo Nobel N.V., Arnhem, Netherlands

[21] Appl. No.: 310,357

[22] Filed: Sep. 21, 1994

Related U.S. Application Data

[63] Continuation of Ser. No. 102,865, Aug. 6, 1993, abandoned, which is a continuation of Ser. No. 904,075, Jun. 18, 1992, abandoned.

[30] Foreign Application Priority Data

Jun. 18, 1991 [EP] European Pat. Off. ............. 91201523

[51] Int. Cl.$^6$ .............................. C12N 5/10; C12N 1/15; C12N 1/19; C12N 1/21
[52] U.S. Cl. ................ 435/240.1; 435/69.3; 435/240.2; 435/240.4; 435/252.3; 435/252.31; 435/252.33; 435/252.34; 435/254.11; 435/254.2; 435/254.21; 435/320.1; 536/235; 536/237
[58] Field of Search ........................... 435/69.3, 252.3, 435/320.1, 240.1, 240.2, 240.4, 252.31, 252.33, 252.34, 254.11, 254.2, 244.21; 536/23.7, 23.5

[56] References Cited

U.S. PATENT DOCUMENTS

| 4,554,101 | 11/1985 | Hopp . |
| 4,639,732 | 1/1987 | Murray et al. . |
| 4,710,377 | 12/1987 | Schenkel et al. . |
| 4,874,705 | 10/1989 | Andrews et al. . |
| 4,879,213 | 11/1989 | Fox et al. . |
| 5,028,694 | 7/1991 | Mewman et al. . |
| 5,273,901 | 12/1993 | Jacobson et al. . |
| 5,279,960 | 1/1994 | Anderson et al. . |

FOREIGN PATENT DOCUMENTS

| 0223710 | 5/1987 | European Pat. Off. . |
| 0328253 | 8/1989 | European Pat. Off. . |
| 0390267 | 10/1990 | European Pat. Off. . |
| WO92/04460 | 3/1992 | WIPO . |

OTHER PUBLICATIONS

C.A. Sutton, "Characterization of coccidial proteins by two–dimensional sodium dodecyl sulphate–polycrylamide gel electrophoresis," Parasitology, (1989), 99, 174–187. Great Britain.

H.D. Danforth et al., "Dose and Boost Dependency of Genetically Engineered Antigens in the Development of Protection in Outbred and Congenic Chickens to Coccidial Challege," The American Society of Parasitologists, Abstract 30.

J. Ellis et al., "Development of a Genetically Engineered Vaccine Against Poultry Coccidiosis," Parasitology Today, vol. 7, No. 12, 1991, pp. 344–346.

M.C. Jenkins, "A cDNA encoding a merozoite surface protein of the protozoan Eimeria acervulina contains tandem–repeated sequences," Nucleic Acids Research, vol. 16, No. 20, p. 9863.

C. Monahan et al., "Vaccination of ponies with Stongylus vulgaris irradiated larvae, adult, worm, somatic antigens, or larval somatic antigens plus excretory/secretory products" The American Society of Parasitologists, 84.

M.D. Castle, "Characterization of a Recombinant Eimeria acervulina Antigen Expressed in Sporozoite and Merozoite Developmental Stages," J. Parasitol 77(3), 1991, oo 384–390.

M.C. Jenkins et al., "Eimeria acervulina : Cloning of a cDNA Encoding an Immunogenic Region of Several Related Merozoite Surface and Rhoptry Proteins" Experimental Parasitology, 70, pp. 353–262 (1990).

Derwent Abstract No. 89–270713, Jenkins et al. 1989.

Derwent Abstract No. 88–360965, J.B. Dame et al. 1988.

Young and Davis PNAS 80: 1194–1198 1983.

Guo et al. Gene 29: 251–254 1984.

Kim et al. Infect. Immun. 57(8): 2434–2440 1989.

Stern. Tibtech 9: 163–167 1991.

Berzofsky. Science 229: 932–940 1985.

Jenkins et al. Mol. and Biochem. Parasitol. 25:155–164. 1987.

Bowie et al. Science 247: 1306 1990.

Wallach et al. Infection and Immunity 58(2): 557–62 1990.

Kumar et al. PNAS 87: 1337–1341 Feb. 1990.

Sigma Catalog 1990 pp. 1546–1548.

Primary Examiner—Anthony C. Caputa
Attorney, Agent, or Firm—Mary E. Gormley

[57] ABSTRACT

The invention is concerned with novel Eimeria proteins with immunogenic properties as well as with DNA sequences encoding these proteins. These proteins can be administered to chickens thereby protecting the chickens against coccidiosis. In addition the DNA encoding these proteins can be used for the preparation of a vector vaccine against coccidiosis.

20 Claims, 10 Drawing Sheets

DNA ENCODING AN EIMERIA 50 KD ANTIGEN

This is a continuation of U.S. Ser. No. 08/102,865, filed Aug. 6, 1993, now abandoned, which is a file wrapper continuation of U.S. Ser. No. 07/904,075, filed Jun. 18, 1992, now abandoned.

The present invention is concerned with a protein having one or more immunogenic determinants of an Eimeria antigen, a nucleic acid sequence encoding this protein, a recombinant vector molecule or recombinant vector virus comprising such a nucleic acid sequence, a host cell transformed with such a recombinant vector molecule or infected with the recombinant vector virus, antibodies immunoreactive with said protein, as well as a vaccine for the protection of avians against coccidiosis.

BACKGROUND OF THE INVENTION

Coccidiosis is a disease which is caused by intracellular parasites, protozoa, of the subphylum Apicomplexa and the genus Eimeria. These parasites multiply in cells which form part of the gastro-intestinal tract and digestive organs.

Due to the increase in intensive production, the damage which is caused by these parasites in the poultry industry has risen alarmingly in recent decades. For example, the losses which poultry farmers in the Netherlands suffer every year run into millions of guilders; the loss in 1986 was about 13 million guilders; in the same year a loss of U.S. $ 300 million was suffered in the U.S., despite the use of coccidiostats.

The pathogens of coccidiosis in chickens can be subdivided into nine different species, i.e. *Eimeria acervulina, E. maxima, E. tenella, E. necatrix, E. brunetti, E. mitis, E. praecox, E. mivati* and *E. hagani*. However, some people doubt the existence of the last two species. All of these species have only the chicken as host and display a high degree of tissue specificity. The life cycles of the said species are, however, similar.

The species do differ in their pathogenic effect on chickens, the type of chicken also playing a role; thus, a broiler chicken will be subjected to a great deal of damage by a parasite such as *E. acervulina* or *E. maxima* because these parasitise large portions of the small intestine, where food digestion plays a major role.

During the life cycle, the Eimeria parasites pass through a number of stages. The infectious stage (the sporulating oocyst) is taken in orally and passes into the stomach of the chicken, where the wall of the cyst bursts open as a result of the grinding action. The four sporocysts, which this oocyst contains, are released and pass into the duodenum, where they are exposed to bile and digestive enzymes. As a result, an opening is made in the sporocyst wall and the sporozoites present in the sporocyst are released. These sporozoites are mobile and search for suitable host cells, epithelium cells, in order to penetrate and to reproduce. Depending on the species, this first reproduction phase lasts 20 to 48 hours and several tens to hundreds of merozoites are formed, which each again penetrate a new host cell and reproduce. After two to sometimes five of these asexual reproduction cycles, depending on the species the intracellular merozoites grow into sexual forms, the male and female gametocytes. After fertilization of the female by a male gamete, a zygote is formed which creates a cyst wall about itself. This oocyst leaves the host cell and is driven out with the faeces. If the temperature and humidity outside the chicken are relatively high and, at the same time, there is sufficient oxygen in the air, the oocyst can sporulate to the infectious stage.

Thus, no intermediate host is needed for transfer of the parasite from chicken to chicken. It is therefore conceivable that with a high degree of occupation of the available surface area the infection pressure in a chicken farm rapidly increases.

The parasite can be combatted in various ways.

In addition to using good management, coccidiosis can be controlled by using coccidiostatic agents which frequently are mixed in the feed or drinking water. However, these agents have suffered a drop in effectiveness in recent years, partly because of the high genetic capacity of the parasite to develop resistance against various combatting agents. In addition, a number of these agents leave residues in the meat which can give rise to problems on consumption.

Immunological prophylaxis would, therefore, constitute a much better combatting method. It is known that chickens which have lived through a sufficiently high infection are able to resist a subsequent contact with the same type of Eimeria. Resistance towards Eimeria can also be induced by infecting the birds several times with low doses of oocysts or with oocysts of weakened (non-pathogenic) strains. However, controlled administration to, specifically, large numbers of broiler chickens is a virtually insurmountable problem in this case.

BRIEF DESCRIPTION OF THE INVENTION

According to the present invention purified proteins having one or more immunogenic determinants of an Eimeria antigen, essentially free from the whole parasite or other protein with which they are ordinarily associated are provided which can be used for the preparation of a vaccine for the immunization of avians, in particular poultry against coccidiosis.

The invention is also concerned with a nucleic acid sequence encoding these proteins, a recombinant vector molecule or recombinant vector virus comprising such a nucleic acid sequence, a host cell transformed with such a recombinant vector molecule or infected with the recombinant vector virus, antibodies immunoreactive with said protein, as well as a vaccine for the protection of avians against coccidiosis.

DETAILED DESCRIPTION OF THE INVENTION

Figure 1A:
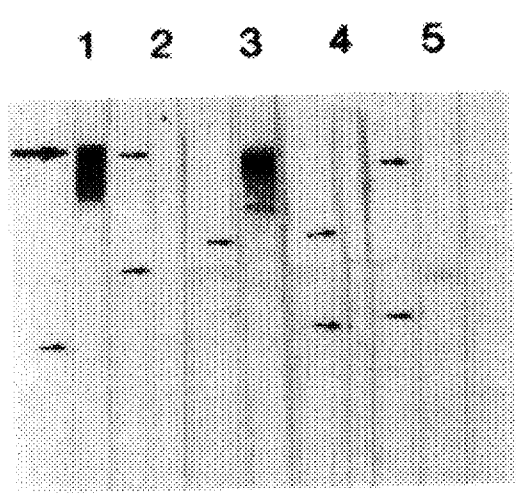
FIG. 1A-1B is a panel of different Eimeria species and stages reacting with monoclonal antibodies E.ACER 11A-2A (Panel A) and E.ACER 12B-2B (Panel B).

"Nucleic acid sequence" as used herein refers to a polymeric form of nucleotides of any length, both to ribonucleic acid sequences and to deoxy ribonucleic acid sequences. In principle, this term refers to the primary structure of the molecule. Thus, this term includes double and single stranded DNA, as well as double and single stranded RNA, and modifications thereof.

In general, the term "protein" refers to a molecular chain of amino acids with a biological activity, does not refer to a specific length of the product and if required can be modified in vivo or in vitro, for example by glycosylation, amidation, carboxylation or phosphorylation; thus inter alia, peptides, oligopeptides and polypeptides are included.

The term "protein having one or more immunogenic determinants of an Eimeria antigen" refers to a protein having one or more epitopes capable of eliciting an immune response against Eimeria parasites in host animals.

The term "molecular weight" is used herein as an apparent size estimation under the circumstances described in the individual examples. The true molecular mass can only be determined after sequencing the full length protein. For individual proteins the apparent molecular weight estimated with SDS-PAGE can be erroneous due to hydrophobicity of the protein, or to the presence of oligosaccharides, lipids (acyl chains) or other interfering substitutes. Even the percentage of acrylamide gel used can influence the mobility in the gel relative to water-soluble marker proteins. An example is described in Frank, R. N. and Rodbard, D. (1975) Arch. Biochem. Biophys. 171, 1–13. Apart from these limitations most of the SDS-PAGE (Western blots) runs performed for this application were carried out non-reduced (so without the addition of beta-mercapthoethanol or dithiotreitol) for purpose of better recognition by Mabs.

In particular, the invention provides proteins having one or more immunogenic determinants of an Eimeria antigen wherein the Eimeria antigen has a molecular weight in SDS-PAGE of about 200, 100, 50 or 20 kD and the Eimeria antigen specifically binds with monoclonal antibody E.ACER 11A-2A or E.ACER 12B-2B, E.ACER 5F-2, E.ACER 10C-2A or E.ACER 10E-2, respectively. Samples of the hybridoma cell lines producing these monoclonal antibodies were deposited with the European Collection of Animal Cell Cultures (ECACC) at Porton Down, UK, under the accession No. 91061223 (E.ACER 12B-2B), 91061222 (E.ACER 11A-2A), 91061219 (E.ACER 5F-2), 91061220 (E.ACER 10C-2A) and 91061221 (E.ACER 10E-2).

The Eimeria antigens disclosed above can be characterized by their isolation procedure, i.e. the antigens are obtainable by:

1. extracting *Eimeria acervulina* parasites with a 2% Triton X114 solution.
2A. applying the hydrophobic fraction obtained after phase separation from step 1. to 1. E.ACER 10C-2A sepharose CL-4B bound immuno-affinity chromatography, or to 2. E.ACER 10E-2 sepharose CL-4B bound immuno-affinity chromatography, or
2B. applying the hydrophilic fraction obtained after phase separation from step 1. to E.ACER 11A-2A sepharose CL-4B bound immuno-affinity chromatography, or
2C. applying the hydrophilic fraction obtained after phase separation from step 1. to E.ACER 5F-2 sepharose CL-4B bound immuno-affinity chromatography,
3. 1. eluting the purified 50, 100 or 200 kD Eimeria protein with 0.1 M glycine/HCl+0.1% NP40 pH 2.6, or
2. eluting the purified 20 kD Eimeria protein with 3M KSCN in 25 mM Tris/HCl+0.5M NaCl+0.1% NP40 pH 8.0.

Preferred proteins according to the invention comprise one or more immunogenic determinants of the *Eimeria acervulina* antigens Eam200, Eam100 or Eas100, Eam45 or Eam20 (Example 2).

Eam200 is an Eimeria protein of about 200 kD purified from *Eimeria acervulina* merozoites and is immuno-reactive with monoclonal antibody (Mab) E.ACER 11A-2A.

Eas100 is an Eimeria protein of about 100 kD purified from *Eimeria acervulina* sporozoites and is immuno-reactive with Mab E.ACER 5F-2. Eam100 is the merozoite equivalent.

Eam45 is an Eimeria protein of about 50 kD purified from *Eimeria acervulina* merozoites and is immuno-reactive with Mab E.ACER 10C-2A.

Eam20 is an Eimeria protein of about 20 kD purified from *Eimeria acervulina* merozoites and is immuno-reactive with Mab E.ACER 10E-2.

Monoclonal antibodies E.ACER 11A-2A and E.ACER 12B-2B are primarily directed against the Eam200 antigen. As is illustrated in FIG. 1 E.ACER 12B-2B recognised this protein in reduced as well as non-reduced form, panel B lanes 1 and 2. E-ACER 11A-2A recognised only the non-reduced form, panel A, lanes 1 and 2.

Both Mabs, however, recognised a set of polypeptides of MW 100 to 200 kD in *E. acervulina* sporozoites and a clear positive band of MW±130 kD in *E. tenella* sporozoites, lanes 3 and 5.

Using fluorescence the cross-reaction to sporozoites was limited to the anterior end of the sporozoite, where the organelles involved in invasion are localised.

*E. tenella* second generation merozoites did not appear to bind these Mabs probably due to the low abundance of the protein in that stage.

Monoclonal antibody E.ACER 10C-2A anti Eam45, only recognised a protein of similar molecular weight in sporozoites of *E. acervulina* and no reaction was found against *E. tenella* as illustrated in FIG. 2 panel A.

E.ACER 10E-2, anti Eam20, also recognised a faint band (MW±20 kD) in sporozoites of the homologous species only, although apart from *E. acervulina* and *E. tenella* no other species were tested, see FIG. 2 panel B.

Monoclonal E.ACER 5F-2 was raised against *E. acervulina* sporozoites but also recognised a protein of±100 kD in merozoites of the homologous species. Reactivity against other species has not been tested.

More particularly, this invention provides examples of proteins having one or more immunogenic determinants of the purified Eimeria antigens identified above. These examples are proteins comprising the amino acid sequence shown in SEQ ID NO. :2, 6, 8 or 10 and its functional variants.

Figure 9:
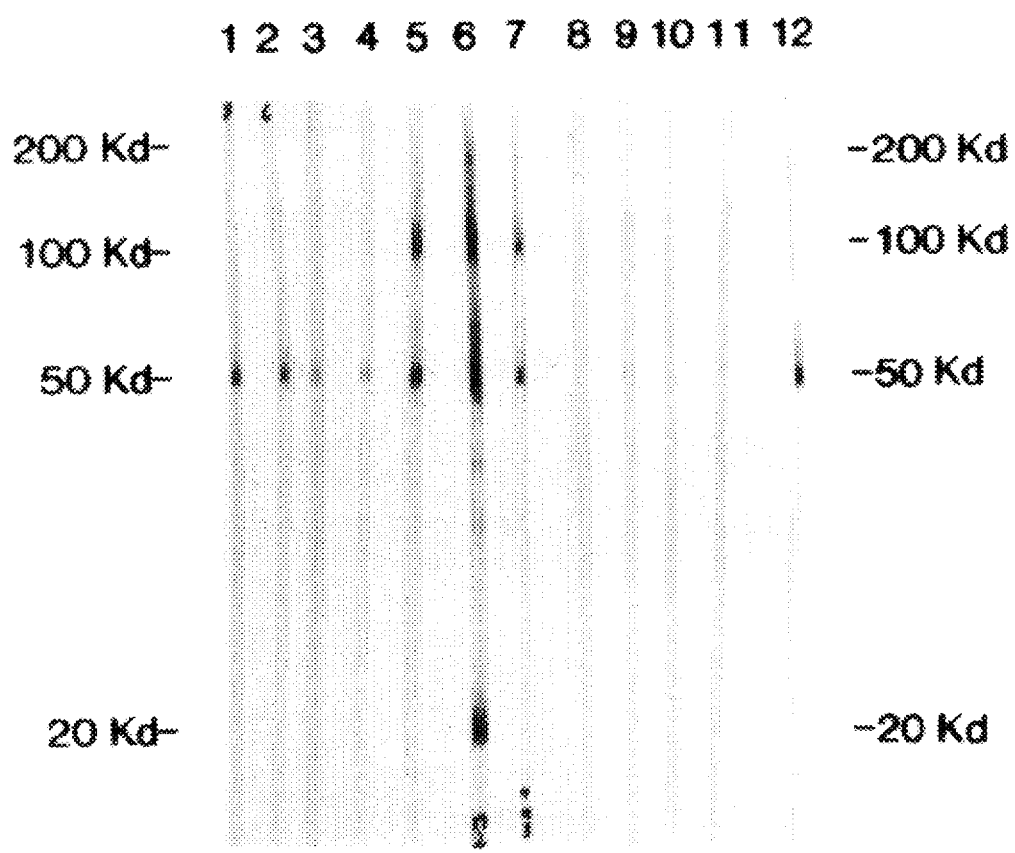
FIG. 9 depicts the reaction of clone Eam45 (M3)-selected antibodies on Western blot strips of *E. acervulina* proteins.

In addition, the present invention provides an Eimeria protein having the amino acid sequence shown in SEQ ID NO. 4 and its functional variant. This protein was identified by screening an Eimeria merozoite CDNA library with anti-Eam45 serum. This serum demonstrated a positive reaction with an about 100 kD protein (in addition to a positive reaction with the about 50 kD protein) when probing this serum back on a merozoite blot (FIG. 9).

The functional variants of the proteins specifically disclosed herein are proteins derived from the above-noted amino acid sequences, for example by deletions, insertions and/or substitutions of one or more amino acids, but retain one or more immunogenic determinants of the Eimeria antigens, i.e. said variants have one or more epitopes capable of eliciting an immune response in a host animal.

It will be understood that for the particular proteins embraced herein, natural variations can exist between individual Eimeria parasites or strains. These variations may be demonstrated by (an) amino acid difference(s) in the overall sequence or by deletions, substitutions, insertions, inversions or additions of (an) amino acid(s) in said sequence. Amino acid substitutions from which can be expected that they do not essentially alter biological and immunological activities, have been described. Amino acid replacements between related amino acids or replacements which have occurred frequently in evolution are, inter alia Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Based on this information Lipman and Pearson developed a method for rapid and sensitive protein comparison (Science 227, 1435–1441, 1985) and determining the functional similarity between homologous proteins.

Furthermore, also immunogenic fragments of the proteins specifically disclosed herein or their functional variants are included in the present invention.

The term "fragment" as used herein means a DNA or amino acid sequence comprising a subsequence of the nucleic acid sequence or protein of the invention. Said fragment is or encodes a polypeptide having one or more immunogenic determinants of an Eimeria antigen. Methods for determining usable immunogenic polypeptide fragments are outlined below. Fragments can inter alia be produced by enzymatic cleavage of precursor molecules, using restriction endonucleases for the DNA and proteases for the polypeptides. Other methods include chemical synthesis of the fragments or the expression of polypeptide fragments by DNA fragments.

Suitable immunogenic polypeptide fragments of a protein according to the invention containing (an) epitope(s) can be found by means of the method described in Patent Application WO 86/06487, Geysen, H. M. et al. (Proc. Natl. Acad. Sci. 81, 3998–4002, 1984), Geysen, H. M. et al. (J. Immunol. Meth. 102, 259–274, 1987) based on the so-called pepscan method, wherein a series of partially overlapping peptides corresponding with partial sequences of the complete polypeptide under consideration, are synthesized and their reactivity with antibodies is investigated.

In addition, a number of regions of the poly-peptide, with the stated amino acid sequence, can be designated epitopes on the basis of theoretical considerations and structural agreement with epitopes which are now known. The determination of these regions is based on a combination of the hydrophilicity criteria according to Hopp and Woods (Proc. Natl. Acad. Sci. 78, 3824–3828, 1981) and the secondary structure aspects according to Chou and Fasman (Advances in Enzymology 47, 45–148, 1987).

T-cell epitopes which may be necessary can likewise be derived on theoretical grounds, e.g. with the aid of Berzofsky's amphiphilicity criterion (Science 235, 1059–62, 1987).

The invention further provides isolated and purified nucleic acid sequences encoding the above-noted proteins of Eimeria.

As is well known in the art, the degeneracy of the genetic code permits substitution of bases in a codon resulting in an other codon but still coding for the same amino acid, e.g. the codon for the amino acid glutamic acid is both GAT and GAA. Consequently, it is clear that for the expression of a protein with the amino acid sequence shown in SEQ ID NO's: 2, 4, 6, 8 or 10 use can be made of a derivate nucleic acid sequence with such an alternative codon composition different from the nucleic acid sequence shown in SEQ ID NO's: 1, 3, 5, 7 or 9 respectively.

Therefore, the present invention particularly provides nucleic acid sequences encoding at least part of the proteins having the amino acid sequence shown in SEQ ID NO's.: 2, 4, 6, 8 or 10 and their functional variants.

The information provided in SEQ ID NO's: 1, 3, 5, 7 and 9 allows a person skilled in the art to isolate and identify the nucleic acid sequences encoding the various functional variant proteins mentioned above having corresponding immunological characteristics with the Eimeria proteins specifically disclosed herein. The generally applied Southern blotting technique or colony hybridization can be used for that purpose (Experiments in Molecular Biology, ed. R. J. Slater, Clifton, U.S.A., 1986; Singer-Sam, J. et al., Proc. Natl., Acad. Sci. 80, 802–806, 1983; Maniatis T. et al., Molecular Cloning, A laboratory Manual, second edition, Cold Spring Harbor Laboratory Press, USA, 1989). For example, a cDNA library derived from a specific Eimeria strain is transferred, or "blotted" onto a piece of nitrocellulose filter. It is now possible to identify specific Eimeria nucleic acid sequences on the filter by hybridization to a defined labeled DNA fragment or "probe", i.e. a (synthetic) poly- or oligonucleotide sequence derived from the nucleic acid sequence shown in SEQ ID NO's: 1, 3, 5, 7 and 9, which under specific conditions of salt concentration and temperature hybridizes to the homologous nucleic acid sequences present on the filter. After washing the filter, hybridized material may be detected by autoradiography. The corresponding DNA fragment can now be eluted from the agarose gel and used to direct the synthesis of a functional variant of the polypeptide disclosed in SEQ ID NO's: 2, 4, 6, 8 or 10.

Typically, a cDNA library from Eimeria can be constructed exactly according to the procedure described in Example 3. The inserts from clones pGEM4Z Eam200, pGEM4Z Eam45 M1(E), pGEM4Z Eam45 M3(E) pGEM4Z Eam20 (E) or pGEM4Z Eam100E can be labeled with digoxigenin-dUTP by random priming, exactly following the protocol going with the "DNA labelling and detection kit, non-radioactive" from Boehringer, Mannheim (Cat. No. 1093657).

Filters containing immobilized DNA from the Eimeria cDNA library described above can be prepared as described by Maniatis et al., supra and probed by the freshly denatured (10 min. 95° C.), labeled Eimeria fragment for 16 hours at 42° C. according to the manufacturer's instructions. Filters are then washed as follows: twice for fifteen minutes with 2×SSC, 0.1% (w/v) SDS (1×SSC is 0.015 mol/l sodium citrate pH 7.0 plus 0.15 mol/l NaCl) at room temperature and twice for fifteen minutes with 1×SSC, 0.1% (w/v) SDS at 55° C. For final identification filters are then washed twice with PBS-tween (7.65 g/l NaCl, 0.91 g/l $Na_2HPO_4.2H_2O$, 0.21 g/l $KH_2PO_4$, 0.05% (v/v) Tween 80, pH 7.3) for 15 minutes at room temperature. The filters were then reacted with a 1:5000 dilution in PBS-tween of polyclonal sheep anti-digoxigenin Fab-fragments, conjugated to alkaline phosphatase, for thirty minutes at room temperature. After washing the filters for four times fifteen minutes with PBS-tween at room temperature and once for fifteen minutes with 0.01M Tris-HCl pH 8.0, 0.15M NaCl, binding of the alkaline phosphatase to the filters was detected upon incubation with a solution of 0.33 g/l Nitroblue tetrazolium and 0.17 g/l 5-bromo-4-chloro-3-indolyl-phosphate in 0.1M Tris-HCl pH 9.6, 0.1M NaCl, 0.01M $MgCl_2$. The DNA that reacts with the probe can be used to express the encoding polypeptide as outlined below.

Thereafter, the polypeptide can be assayed for the presence of one or more immunogenic determinants of an Eimeria antigen protein according to one of the following methods.

The polypeptide can be purified from the *E. coli* lysate by methods known in the art, such as salt fractionation, ionic exchange chromatography, hydrophobic interaction chromatography, or metal chelate chromatography. The purified product can be used to raise monospecific antibodies as described below. The antibodies can be probed back onto Western blots of parasite material such as merozoites or sporozoites. Positive signals connect the product of the *E. coli* translation directly to the parasite protein.

Another possibility to achieve this is the anti-body select technique binding antibodies directly to a filter containing a monoculture of recombinant phages in *E. coli* expressing the Eimeria DNA insert. By eluting these bound antibodies using the procedure of Osaki et al (J. Immunological Methods 89, 213–219, 1986) and allowing them to bind again to Western blots of Eimeria antigens the connection is a fact. The latter procedure was followed for the Eas100 and the Eam45 clones (Example 3, FIGS. 8 and 9).

The hybridization techniques described above may also be used in order to arrive at full length clones in case only a portion of the total coding sequence has been identified. In particular clone pGEM4Z Eam200 and pGEM4Z Eam100E may be used to screen cDNA or genomic DNA libraries for possible additional coding sequence. Another method to extend DNA sequences is the "semi-specific" polymerase chain reaction outlined in Example 3.

Therefore, a nucleic acid sequence encoding a functional variant of the proteins disclosed herein encodes a polypeptide comprising one or more immunogenic determinants of an Eimeria antigen and hybridizes to the DNA sequence shown in SEQ ID NO's: 1, 3, 5, 7 or 9.

In another way Eimeria cDNA may be cloned into a λgt11 phage as described by Huynh et al. (In: D. Glover (ed.), DNA Cloning: A Practical Approach, IRL Press Oxford, 49–78, 1985) and expressed into a bacterial host. Recombinant phages can then be screened with polyclonal serum raised against the purified Eimeria proteins described above or in SEQ ID NO's: 2, 4, 6, 8 or 10 determining the presence of corresponding immunological regions of the variant polypeptide. The production of the polyclonal serum to be used herein elicited against the Eimeria proteins is described below.

More particularly, the present invention comprises nucleic acid sequences encoding a protein having one or more immunogenic determinants of an Eimeria antigen, wherein the nucleic acid sequences contain at least part of the DNA sequences shown in SEQ ID NO's: 1, 3, 5, 7 or 9, respectively.

A nucleic acid sequence according to the invention may be isolated from a particular Eimeria strain and multiplied by recombinant DNA techniques including polymerase chain reaction (PCR) technology or may be chemically synthesized in vitro by techniques known in the art.

A nucleic acid sequence according to the present invention can be ligated to various replication effecting DNA sequences with which it is not associated or linked in nature resulting in a so called recombinant vector molecule which can be used for the transformation of a suitable host. Useful recombinant vector molecules, are preferably derived from, for example plasmids, bacteriophages, cosmids or viruses.

Specific vectors or cloning vehicles which can be used to clone nucleic acid sequences according to the invention are known in the art and include inter alia plasmid vectors such as pBR322, the various pUC, PGEM and Bluescript plasmids, bacteriophages, e.g. λgt-Wes, Charon 28 and the M13 derived phages or viral vectors such as SV40, adenovirus or polyoma virus (see also Rodriquez, R. L. and D. T. Denhardt, ed., Vectors: A survey of molecular cloning vectors and their uses, Butterworths, 1988; Lenstra, J. A. et al., Arch. Virol. 110, 1–24, 1990). The methods to be used for the construction of a recombinant vector molecule according to the invention are known to those of ordinarily skill in the art and are inter alia set forth in Maniatis, T. et al. (Molecular Cloning A Laboratory Manual, second edition; Cold Spring Harbor Laboratory, 1989).

For example, the insertion of the nucleic acid sequence according to the invention into a cloning vector can easily be achieved when both the genes and the desired cloning vehicle have been cut with the same restriction enzyme(s) as complementary DNA termini are thereby produced.

Alternatively, it may be necessary to modify the restriction sites that are produced into blunt ends either by digesting the single-stranded DNA or by filling in the single-stranded termini with an appropriate DNA polymerase. Subsequently, blunt end ligation with an enzyme such as T4 DNA ligase may be carried out.

If desired, any restriction site may be produced by ligating linkers onto the DNA termini. Such linkers may comprise specific oligonucleotide sequences that encode restriction site sequences. The restriction enzyme cleaved vector and nucleic acid sequence may also be modified by homopolymeric tailing.

"Transformation", as used herein, refers to the introduction of a heterologous nucleic acid sequence into a host cell, irrespective of the method used, for example direct uptake or transduction. The heterologous nucleic acid sequence may be maintained through autonomous replication or alternatively, may be integrated into the host genome. If desired, the recombinant vector molecules are provided with appropriate control sequences compatible with the designated host which can regulate the expression of the inserted nucleic acid sequence. In addition to microorganisms, cell cultures derived from multi-cellular organisms may also be used as hosts.

The recombinant vector molecules according to the invention preferably contain one or more marker activities that may be used to select for desired transformants, such as ampicillin and tetracycline resistance in pBR322, ampicillin resistance and α-peptide of β-galactosidase in pUC8.

A suitable host cell is a microorganism or cell which can be transformed by a nucleic acid sequence encoding a polypeptide or by a recombinant vector molecule comprising such a nucleic acid sequence and which can if desired be used to express said polypeptide encoded by said nucleic acid sequence. The host cell can be of procaryotic origin, e.g. bacteria such as *Escherichia coli, Bacillus subtilis* and *Pseudomonas* species; or of eucaryotic origin such as yeasts, e.g. *Saccharomyces cerevisiae* or higher eucaryotic cells such as insect, plant or mammalian cells, including HeLa cells and Chinese hamster ovary (CHO) cells. Insect cells include the Sf9 cell line of *Spodoptera frugiperda* (Luckow et al., Bio-technology 6, 47–55, 1988). Information with respect to the cloning and expression of the nucleic acid sequence of the present invention in eucaryotic cloning systems can be found in Esser, K. et al. (Plasmids of Eukaryotes, Springer-Verlag, 1986).

In general, prokaryotes are preferred for the construction of the recombinant vector molecules useful in the invention. For example *E. coli* K12 strains are particularly useful such as DH5α or MC1061λ.

For expression nucleic acid sequences of the present invention are introduced into an expression vector, i.e. said sequences are operably linked to expression control sequences. Such control sequences may comprise promoters, enhancers, operators, inducers, ribosome binding sites etc. Therefore, the present invention provides a recombinant vector molecule comprising a nucleic acid sequence encoding an Eimeria protein identified above operably linked to expression control sequences, capable of expressing the DNA sequences contained therein in (a) transformed host cell(s).

It should, of course, be understood that the nucleotide sequences inserted at the selected site of the cloning vector may include nucleotides which are not part of the actual structural gene for the desired polypeptide or may include only a fragment of the complete structural gene for the desired protein as long as transformed host will produce a polypeptide having at least one or more immunogenic determinants of an Eimeria antigen.

When the host cells are bacteria, illustrative useful expression control sequences include the Trp promoter and operator (Goeddel, et al., Nucl. Acids Res. 8, 4057, 1980); the lac promoter and operator (Chang, et al., Nature 275, 615, 1978); the outer membrane protein promoter (Nakamura, K. and Inouge, M., EMBO J. 1, 771–775, 1982); the bacteriophage λpromoters and operators (Remaut, E. et al., Nucl. Acids Res. 11, 4677–4688, 1983); the α-amylase (B. subtilis) promoter and operator, termination sequence and other expression enhancement and control sequences compatible with the selected host cell. When the host cell is yeast, illustrative useful expression control sequences include, e.g., α-mating factor. For insect cells the polyhedrin or p10 promoters of baculoviruses can be used (Smith, G. E. et al., Mol. Cell. Biol. 3, 2156–65, 1983). When the host cell is of mammalian origin illustrative useful expression control sequences include, e.g., the SV-40 promoter (Berman, P. W. et al., Science 222, 524–527, 1983) or, e.g. the metallothionein promoter (Brinster, R. L., Nature 296, 39–42, 1982) or a heat shock promoter (Voellmy et al., Proc. Natl. Acad. Sci. USA 82, 4949–53, 1985). Alternatively, also expression control sequences present in Eimeria may be applied. For maximizing gene expression, see also Roberts and Lauer (Methods in Enzymology 68, 473, 1979).

Therefore, the invention also comprises (a) host cell(s) transformed with a nucleic acid sequence or recombinant expression vector molecule described above, capable of producing the Eimeria protein by expression of the nucleic acid sequence.

Immunization of avians against Eimeria infection can, for example be achieved by administering to the animals a protein according to the invention in an immunologically relevant context as a so-called subunit vaccine. The subunit vaccine according to the invention may comprise a protein in a pure form, optionally in the presence of a pharmaceutically acceptable carrier. The protein can optionally be covalently bonded to a non-related protein, which, for example can be of advantage in the purification of the fusion product. Examples are β-galactosidase, protein A, prochymosine, blood clotting factor Xa, etc.

In some cases the ability to raise protective immunity using these proteins per se may be low. Small fragments are preferably conjugated to carrier molecules in order to raise their immunogenicity. Suitable carriers for this purpose are macromolecules, such as natural polymers (proteins like key hole limpet hemocyanin, albumin, toxins), synthetic polymers like polyamino acids (polylysine, poly-alanine), or micelles of amphiphilic compounds like saponins. Alternatively these fragments may be provided as polymers thereof, preferably linear polymers.

Proteins to be used in such subunit vaccines can be prepared by methods known in the art, e.g. by isolating said polypeptides from Eimeria parasites, by recombinant DNA techniques or by chemical synthesis.

If required the proteins according to the invention to be used in a vaccine can be modified in vitro or in vivo, for example by glycosylation, amidation, carboxylation or phosphorylation.

An alternative to subunit vaccines are live vector vaccines. A nucleic acid sequence according to the invention is introduced by recombinant DNA techniques into a micro-organism (e.g. a bacterium or virus) in such a way that the recombinant micro-organism is still able to replicate thereby expressing a polypeptide coded by the inserted nucleic acid sequence and eliciting an immune response in the infected host animal.

A preferred embodiment of the present invention is a recombinant vector virus comprising a heterologous nucleic acid sequence described above, capable of expressing the DNA sequence in (a) host cell(s) or host animal infected with the recombinant vector virus. The term "heterologous" indicates that the nucleic acid sequence according to the invention is not normally present in nature in the vector virus.

Furthermore, the invention also comprises (a) host cell(s) or cell culture infected with the recombinant vector virus, capable of producing the Eimeria protein by expression of the nucleic acid sequence.

For example the well known technique of in vivo homologous recombination can be used to introduce a heterologous nucleic acid sequence, e.g. a nucleic acid sequence according to the invention into the genome of the vector virus.

First, a DNA fragment corresponding with an insertion region of the vector genome, i.e. a region which can be used for the incorporation of a heterologous sequence without disrupting essential functions of the vector such as those necessary for infection or replication, is inserted into a cloning vector according to standard recDNA techniques. Insertion-regions have been reported for a large number of micro-organisms (e.g. EP 80,806, EP 110,385, EP 83,286, EP 314,569, WO 88/02022, WO 88/07088, U.S. Pat. No. 4,769,330 and U.S. Pat. No. 4,722,848).

Second, if desired, a deletion can be introduced into the insertion region present in the recombinant vector molecule obtained from the first step. This can be achieved for example by appropriate exonuclease III digestion or restriction enzyme treatment of the recombinant vector molecule from the first step.

Third, the heterologous nucleic acid sequence is inserted into the insertion-region present in the recombinant vector molecule of the first step or in place of the DNA deleted from said recombinant vector molecule. The insertion region DNA sequence should be of appropriate length as to allow homologous recombination with the vector genome to occur. Thereafter, suitable cells can be infected with wild-type vector virus or transformed with vector genomic DNA in the presence of the recombinant vector molecule containing the insertion flanked by appropriate vector DNA sequences whereby recombination occurs between the corresponding regions in the recombinant vector molecule and the vector genome. Recombinant vector progeney can now be produced in cell culture and can be selected for example genotypically or phenotypically, e.g. by hybridization, detecting enzyme activity encoded by a gene co-integrated along with the heterologous nucleic acid sequence, or detecting the antigenic heterologous polypeptide expressed by the recombinant vector immunologically.

Next, this recombinant micro-organism can be administered to poultry for immunization whereafter it maintains itself for some time, or even replicates in the body of the inoculated animal, expressing in vivo a polypeptide coded for by the inserted nucleic acid sequence according to the invention resulting in the stimulation of the immune system of the inoculated animal. Suitable vectors for the incorporation of a nucleic acid sequence according to the invention can be derived from viruses such as pox viruses, e.g. vaccinia virus (EP 110,385, EP 83,286, U.S. Pat. No. 4,769, 330 and U.S. Pat. No. 4,722,848) or fowl pox virus (WO 88/02022), herpes viruses such as HVT (WO 88/07088) or Marek's Disease virus, adeno virus or influenza virus, or bacteria such as $E.\ coli$ or specific Salmonella species. With recombinant microorganisms of this type, the polypeptide synthesized in the host animal can be exposed as a surface antigen. In this context fusion of the said polypeptide with OMP proteins, or pilus proteins of for example $E.\ coli$ or synthetic provision of signal and anchor sequences which are recognized by the organism are conceivable. It is also possible that the said immunogenic polypeptide, if desired as part of a larger whole, is released inside the animal to be immunized. In all of these cases it is also possible that one or more immunogenic products will find expression which generate protection against various pathogens and/or against various antigens of a given pathogen.

A vector vaccine according to the invention can be prepared by culturing a recombinant bacterium or a host cell infected with a recombinant vector virus comprising a nucleic acid sequence according to the invention, whereafter recombinant bacteria or virus containing cells and/or recombinant vector viruses grown in the cells can be collected, optionally in a pure form, and formed to a vaccine optionally in a lyophilized form.

Host cells transformed with a recombinant vector molecule according to the invention can also be cultured under conditions which are favourable for the expression of a polypeptide coded by said nucleic acid sequence. Vaccines may be prepared using samples of the crude culture, host cell lysates or host cell extracts, although in another embodiment more purified polypeptides according to the invention are formed to a vaccine, depending on its intended use. In order to purify the polypeptides produced, host cells transformed with a recombinant vector according to the invention are cultured in an adequate volume and the polypeptides produced are isolated from such cells or from the medium if the protein is excreted. Poly-peptides excreted into the medium can be isolated and purified by standard techniques, e.g. salt fractionation, centrifugation, ultrafiltration, chromatography, gel filtration or immuno affinity chromatography, whereas intra cellular polypeptides can be isolated by first collecting said cells, disrupting the cells, for example by sonication or by other mechanically disruptive means such as French press followed by separation of the polypeptides from the other intra cellular components and forming the polypeptides to a vaccine. Cell disruption could also be accomplished by chemical (e.g. EDTA or detergents such as Triton X114) or enzymatic means such as lysozyme digestion.

Antibodies or antiserum directed against a poly-peptide according to the invention have potential use in passive immunotherapy, diagnostic immunoassay's and generation of anti-idiotype antibodies.

The Eimeria proteins as characterized above can be used to produce antibodies, both polyclonal, monospecific and monoclonal. If polyclonal antibodies are desired, techniques for producing and processing polyclonal sera are known in the art (e.g. Mayer and Walter, eds, Immunochemical Methods in Cell and Molecular Biology, Academic Press, London, 1987). In short, a selected mammal, e.g. rabbit is given (multiple) injections with above-mentioned immunogens, about 20 µg to about 80 µg of protein per immunization. Immunizations are given with an acceptable adjuvant, generally equal volumes of immunogen and adjuvant. Acceptable adjuvants include Freund's complete, Freund's incomplete, alum-precipitate or water-in-oil emulsions, with Freund's complete adjuvant being preferred for the initial immunization. Freund's incomplete adjuvant is preferred for all booster immunizations. The initial immunization consists of the administration of about 1 ml of emulsion at multiple subcutaneous sites on the backs of the rabbits. Booster immunizations utilizing an equal volume of immunogen are given at about one month intervals and are continued until adequate levels of antibodies are present in an individual rabbits serum. Blood is collected and serum isolated by methods known in the art.

Monospecific antibodies to the immunogen are affinity purified from polyspecific antisera by a modification of the method of Hall et al. (Nature 311, 379–387 1984), prepared by immunizing rabbits as described above with the purified proteins. Monospecific antibody as used herein is defined as a single antibody species or multiple antibody species with homogeneous binding characteristics for the relevant antigen. Homogeneous binding as used herein refers to the ability of the antibody species to bind to a specific antigen or epitope.

Monoclonal antibody reactive against the Eimeria immunogens can be prepared by immunizing inbred mice, preferably Balb/c with the appropriate protein. The mice are immunized intraperitoneally with about 100 ng to about 10 µg immunogen per 0.5 ml dose in an equal volume of an acceptable adjuvant. Such acceptable adjuvants include Freund's complete, Freund's incomplete, alum-precipitate and water-in-oil emulsions. The mice are given intravenous booster immunizations of an equal amount of the immunogen without adjuvant at about days 14, 21 and 63 post primary immunization. At about day three after the final booster immunization individual mice are serologically tested for anti-immunogen antibodies. Spleen cells from antibody producing mice are isolated and fused with murine myeloma cells, such as SP-2/0 or the like, by techniques known in the art (Kohler and Milstein, Nature 256; 495–497, 1975). Hybridoma cells are selected by growth in hypoxanthine, thymidine and aminopterin in an appropriate cell culture medium such as Dulbecco's modified Eagle's medium (DMEM). Antibody producing hybridomas are cloned, preferably using the soft agar technique of MacPherson, (Soft Agar Techniques, Tissue Culture Methods and Applications, Kruse and Paterson, eds., Academic Press, 276, 1973). Discrete colonies are transferred into individual wells of culture plates for cultivation in an appropriate culture medium. Antibody producing cells are identified by screening with the appropriate immunogen. Immunogen positive hybridoma cells are maintained by techniques known in the art. Specific anti-monoclonal antibodies are produced by cultivating the hybridomas in vitro or preparing ascites fluid in mice following hybridoma injection by procedures known in the art.

Anti-idiotype antibodies are immunoglobulins which carry an "internal image" of the antigen of the pathogen against which protection is desired and can be used as an immunogen in a vaccine (Dreesman et al., J. Infect. Disease 151, 761, 1985). Techniques for raising anti-idiotype antibodies are known in the art (MacNamara et al., Science 226, 1325, 1984).

The vaccine according to the invention can be administered in a convential active immunization scheme: single or repeated administration in a manner compatible with the dosage formulation and in such amount as will be prophylactically effective, i.e. the amount of immunizing antigen or recombinant micro-organism capable of expressing said antigen that will induce immunity in avians against challenge by virulent Eimeria parasites. Immunity is defined as the induction of a significant level of protection in a population of chickens after vaccination compared to an unvaccinated group.

For live viral vector vaccines the dose rate per chicken may range from $10^5-10^8$ pfu.

A typical subunit vaccine according to the invention comprises 1 µg–1 mg of the protein according to the invention.

The administration of the vaccine can be done, e.g. intradermally, subcutaneously, intramuscularly, intraperitoneally, intravenously, orally or intranasally.

Additionally the vaccine may also contain an aqueous medium or a water containing suspension, often mixed with other constituents, e.g. in order to increase the activity and/or shelf life. These constituents may be salts, pH buffers, stabilizers (such as skimmed milk or casein hydrolysate), emulsifiers adjuvants to improve the immune response (e.g. oils, muramyl dipeptide, aluminiumhydroxide, saponin, polyanions and amphipatic substances) and preservatives.

It is clear that a vaccine according to the invention may also contain immunogens related to other pathogens of poultry or may contain nucleic acid sequences encoding these immunogens, like antigens of Marek's Disease virus (MDV), Newcastle Disease virus (NDV), Infectious Bronchitis virus (IBV), Infectious Bursal Disease virus (IBDV), Chicken Anemia Agent (CAA), Reo virus, Avian Retro virus, Fowl Adeno virus, Turkey Rhinotracheitis virus, *E. coli* or other Eimeria species to produce a multivalent vaccine.

The invention also relates to an "immunochemical reagent", which reagent comprises a protein according to the invention.

The term "immunochemical reagent" signifies that the protein according to the invention is bound to a suitable support or is provided with a labelling substance.

The supports which can be used are, for example, the inner wall of a microtest well or a cuvette, a tube or capillary, a membrane, filter, test strip or the surface of a particle such as, for example, a latex particle, an erythrocyte, a dye sol, a metal sol or metal compound as sol particle.

Labelling substances which can be used are, inter alia, a radioactive isotope, a fluorescent compound, an enzyme, a dye sol, metal sol or metal compound as sol particle.

A nucleic acid sequence according to the invention can also be used to design specific probes for hybridization experiments for the detection of Eimeria related nucleic acids in any kind of tissue.

The present invention also comprises a test kit comprising said nucleic acid sequence useful for the diagnosis of Eimeria infection.

The invention also relates to a test kit to be used in an immuno-assay, this test kit containing at least one immunochemical reagent according to the invention.

The immunochemical reaction which takes place using this test kit is preferably a sandwich reaction, an agglutination reaction, a competition reaction or an inhibition reaction.

For carrying out a sandwich reaction, the test kit can consist, for example, of a polypeptide according to the invention bonded to a solid support, for example the inner wall of a microtest well, and either a labelled polypeptide according to the invention or a labelled anti-antibody.

Example 1
Preparation and Isolation of Parasites

*E. acervulina* Houghton strain was obtained from the AFRC Houghton Laboratory and was passaged through coccidia-free chickens.

Preparation of parasites and fractions thereof E. tenella parasites were maintained and oocysts were isolated according to methods described by Long et al. (Fol. Vet. Lat. 6, 201–217, 1976). Sporozoites were isolated and purified as described by Wisher & Rose (Parasitology 88, 515–519, 1984) with an additional nylon wool purification as described by Larsen, et al. (J. Parasitol. 70, 597–601, 1984).

Merozoites were harvested at 72 hours after inoculation as follows (see also Jenkins and Dame, Mol. Biochem. Parasitol. 25, 155–164, 1987): Four to six week old chickens were orally infected with $1-5\times10^6$ sporulated oocysts. 72 hrs after inoculation the birds were killed and the duodenum was removed until the Meckels diverticulum and kept in icecold phosphate buffered saline (0.04M PBS pH 7.3). The duodenum was cut lengthwise and washed with icecold PBS. The gut was then cut into 5 cm pieces and suspended in Hanks-BSS containing 100–200 U/ml penicillin, 100–200 µg streptomycin/ml at 37° C. for 15–30 min.

The supernate was removed and filtered through 120, 60 and 35 mesh stainless steel sieves. The eluate was centrifuged at 130 g for 8 min. The supernates were collected and merozoites concentrated after centrifugation at 1500 g for 10 min at 4° C.

The concentrated pellets were resuspended in 25 mM Tris-HCl pH 8.0 containing 150 mM NaCl and purified over DE-52 (Whatman) equilibrated in the same buffer. The merozoites were eluting in the non-bound fraction. Yield about $1\times10^9$ merozoites per infected chicken.

Example 2
Purification of Eimeria Antigens
A. Methods
  Triton X114 Extraction
  According to Bordier (Bordier, C., J. Biol. Chem. 256, 1604–1607, 1981) materials:
  precondensed Triton X114 (TX114) (see below),
  10 mM Tris/HCl-150 mM NaCl pH 7. 4 (TBS),
  100 mM PhenylMethylSulfonylFluoride (PMSF) in isopropanol,
  6% sucrose solution in TBS containing 0.06% TX114 (sucrose cushion).

$5\times10^8$ *E. acervulina* merozoites were homogenized per ml of TBS. The mixture was made up to 1 mM PMSF and 10% (v/v) precondensed TX114.

Using mechanical shearing proteins were extracted for at least 2 hours at 0° C. Non-solubilised material was pelleted by centrifugation for 10' at 12.000 g at 4° C. in Eppendorf centrifuge. The supernatant containing solubilised material was layered onto an equal volume of sucrose cushion and incubated at 40° C. for 10 min.

After centrifugation for 10' at 400 g (ambient temperature), the topphase containing hydrophilic material was taken off and extracted once more, layered again on the same sucrose cushion and centrifuged as above.

The combined bottom fraction was kept separate from the remaining topfraction.

If waterphase needed to be completely undone from hydrophobic material the extraction was repeated once more.

All fractions were kept frozen at −70° C. until further analysis.

Precondensation of Triton X114:

20 ml Triton X114 (Serva) was made up to 1 liter with cold TBS pH 7.4 mixed and incubated at 0°–4° C. After complete solubilization the solution was transferred to a 40° C. waterbath. Phase separation was complete after 16 hours. Topphase was removed and replaced by an equal volume of TBS. This procedure was repeated twice. The final bottom phase, called "precondensed TX114", was kept in 100 ml bottle at 4° C. The final TX114 concentration is approximately 20%.

Monoclonal Antibodies

Antibodies were raised in Balb/C mice against E.acervulina merozoites by repeated intraperitoneal inoculations with $10^6$–$10^7$ merozoites.

The respective spleen cells were fused with myeloma P3X63Ag 8.6.5.3. and cloned as described by Schönherr et al. (Develop. biol. Stand. 50, 235–242, 1982).

Screenings were done by an immunofluorescence test on dried, acetone-fixed, merozoites. Highly concentrated monoclonal antibody solutions were prepared in vitro using dialysis modules as culture vessels with continuous medium replacement as described by Schönherr and van Gelder (Animall Cell Biotechnology 3, 337–355).

Immuno-Affinity Chromatography

Activation of affinity matrix:

Sepharose CL-4B (Pharmacia) was activated using Cyanogen Bromide (CNBr) 50 mg/ml in distilled water.

Activation was carried out in a well ventilated hood. The mixture was stirred with a slowly turning magnetic bar and pH was kept on 10.5–11.0 with 4M NaOH for ±30 min. at ambient temperature.

After the reaction had completed the sepharose was washed on a glass-sintered filter with 500 ml cold water and 500 ml cold 0.2M NaHCO$_3$ (coupling buffer). The gel was used immediately for coupling the immunoglobulins.

Coupling of monoclonal IgG to Sepharose Monoclonal antibody was used as highly concentrated supernatant but dialysed extensively against 0.2M NaHCO$_3$ (coupling buffer). Buffer exchange was also done using PD10 columns (Pharmacia) according to the manufacturers protocol. The CNBr-activated sepharose-CL-4B was made up to 2–5 mg/ml MoAb IgG, final concentration and the mixture was stirred end-over-end overnight at 4° C. or 2 hours on ambient temperature. The non-bound fraction was removed and assayed for protein using BCA reagent (Pierce). The Sepharose was washed ten times and subsequently mixed with 1 volume 1M ethanolamine/HCl pH 8.5 end-over-end for 2 hours at ambient temperature. By subsequent washing with four alternating cycles of 200 ml 0.1M Tris/HCl–0.5M NaCl pH 8.0 and 0.1M HAc–0.5M NaCl pH 4.0 non-covalently bound material was removed. The gel was stored at +4° C. in PBS 0.05% azide.

Affinity Purification

Buffers:

A) 25 mM Tris/HCl+0.5M NaCl+0.1% Nonidet P40 (NP40) pH 8.0

B) 0.1M glycine/HCl+0.1% NP40 pH 2.6

C) 0.1M Tris/HCl+0.5M NaCl+0.1% NP40 pH 8.0

D) 3M KSCN in A)

E) 1M Tris/HCl pH 8.0

F) 10 mM Tris/HCl+150 mM NaCl pH 8.0

7 ml Sepharose-IgG was transferred to a Pharmacia C10/20 column equipped with cooling jacket. Ten times diluted TX114 hydrophobic extract (pellet) in buffer A was applied to the column at 0.5 ml/min. and recirculated for 16–20 hours at 8° C. After washing the column with 5–10 bedvolumes of buffer A), direction of flow was inverted followed by elution with 7.5 ml buffer B), 5 ml buffer C), 10 ml buffer A), 7.5 ml buffer D) and 40 ml buffer A).

Acidic fractions (1 ml) were neutralized immediately with 0.1 ml buffer E). KSCN fractions were dialysed overnight against buffer F). All fractions were analysed on SDS-PAGE, immunoblots and for protein contents by BCA assay.

SDS-Polyacrylamide Gel Electrophoresis (SDS-PAGE) and Immunoblotting

SDS-PAGE was performed on 12% acrylamide gels using the Laemmli buffer system (Laemmli, U. K., Nature 227, 680–685, 1970). Western blotting was carried out according to Vermeulen et al (Vermeulen, A. N. et al., J. Exp. Med. 162, 1460–1476, 1985), using 25x diluted Laemmli lower vessel electrophoresis buffer as blot buffer. Blotting occurred for 1.5 hour at 90 V in a Bio-rad transblot cell.

Nitrocellulose (0.25 μm Schleicher and Schüll) was blocked with 0.1% NFMP (non-fat milk powder (OXOID)) in PBS (0.01M Phosphate in 0.9% saline pH 7.3) for 30 min.

Serum and alkaline phosphatase conjugated anti-serum (Zymed) were incubated for 1.5 hour. Positive binding was detected using BCIP/NBT as substrate.

Polyclonal Antibodies

Rabbit 8275 (K8275) antibodies were raised in rabbits (New Zealand White) by immunisation with E. acervulina 72 hours merozoites in Freund-incomplete like adjuvant emulsion given intradermally twice with 4 weeks interval.

Monospecific antibodies were raised in rabbits previously selected for the absence of anti-Eimeria antibodies in the serum.

Rabbits 5706 and 5792 were injected twice (4–5 wks interval) with 55–100 μg affinity purified Eam45 emulsified with a Freund-incomplete-like (water in oil) adjuvant.

Rabbit 5796 was injected with affinity purified Eam20 according to the same protocol.

Rabbit 5794 was injected with the TX114 hydrophobic extract prior to affinity purification again using the same protocol. This fraction contained Eam45 and Eam20 and some other proteins.

Monospecific antibodies against Eas100 were raised in chickens using the purified protein in 100mM Tris-HCL+150 mM NaCL+0.1% NP40 pH 8.0 emulsified in a Freund's incomplete like adjuvant administered three times subcutaneously in the neck with 14 days intervals. 11 days after the last immunization the chickens were bled and serum was collected (serum from chicken 323 was used for further studies).

B. Results

TX114 extraction

Figure 3:
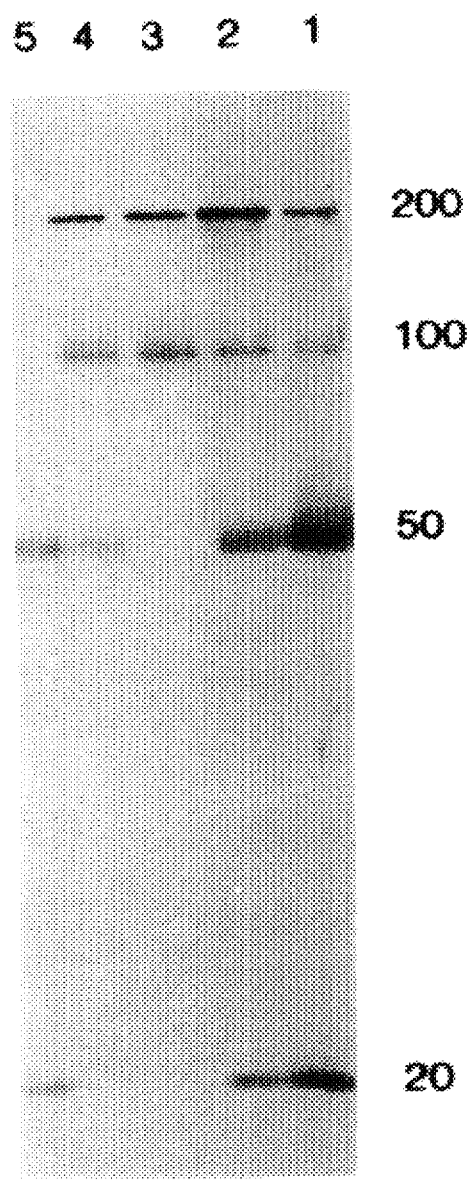
FIG. 3 is a Western blot of different fractions of TX114 extraction of *E. acervulina* merozoites.

FIG. 3 shows the different fractions obtained after TX114 extraction and phase separation. The material was electrophoresed, blotted onto nitrocellulose and probed with a mixture of monoclonal antibodies with specificity for the Eam200, Eam100, Eam45 and Eam20 proteins with respective relative molecular mass of 180–210 kD (mean 200 kD), 95–105 kD (mean 100 kD), 45–55 kD (mean 50 kD) and 18–22 kD (mean 20 kD) determined under non-reducing conditions.

It appeared that Eam200 and Eam100 proteins were of hydrophilic character since they were not present in the hydrophobic pellet (lane 5). Contrarily the Eam45 and Eam20 were absent in the hydrophilic fraction (lane 3).

17

Immuno-Affinity Chromatography of Eam45 and Eam20

Monoclonal antibody E.ACER 10C-2A was coupled to sepharose to bind the Eam45 protein, whereas E.ACER 10E-2 was used to bind Eam20.

Coupling efficiency was over 90% for both MoAbs, leakage of MoAb from the column was minimal.

The "Eam20" column was connected with the "Eam45" column so that the non-bound fraction of the latter was able to bind to the former matrix. Both columns were eluted separately.

Figure 4:
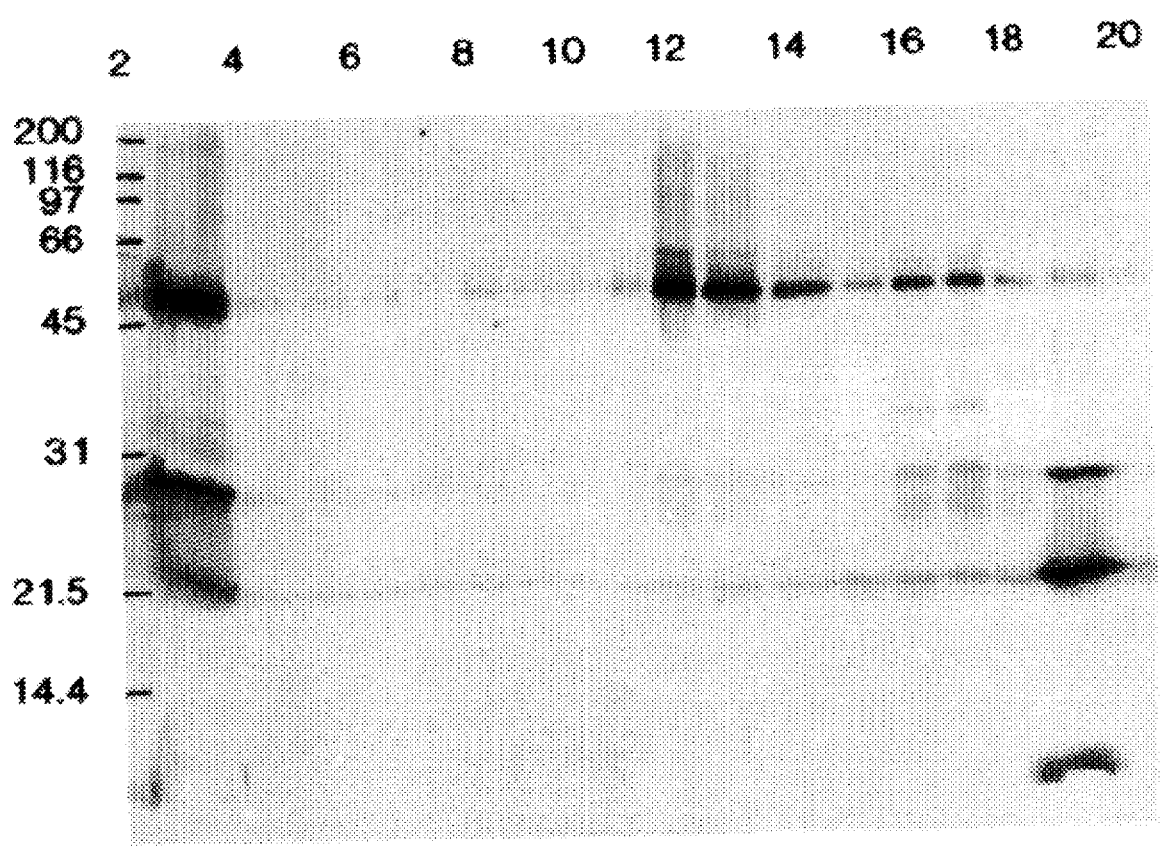
FIG. 4 is a Western blot of different fractions of immunoaffinity purification using E.ACER 10C-2A.

FIG. 4 shows the SDS-PAGE/Immuno blot of the fractions from the 10C-2A (Eam45) matrix. The figure was taken from an experiment different from FIG. 3. The blot was probed with rabbit K8275 antibodies. It appeared that the Eam45 predominantly eluted at pH 2.6 (lanes 12 to 14), although some remained, which eluted with the KSCN (lanes 16 to 18). The latter fractions, however, contained other lower molecular weight material probably not related to the Eam45 antigen.

Figure 5:
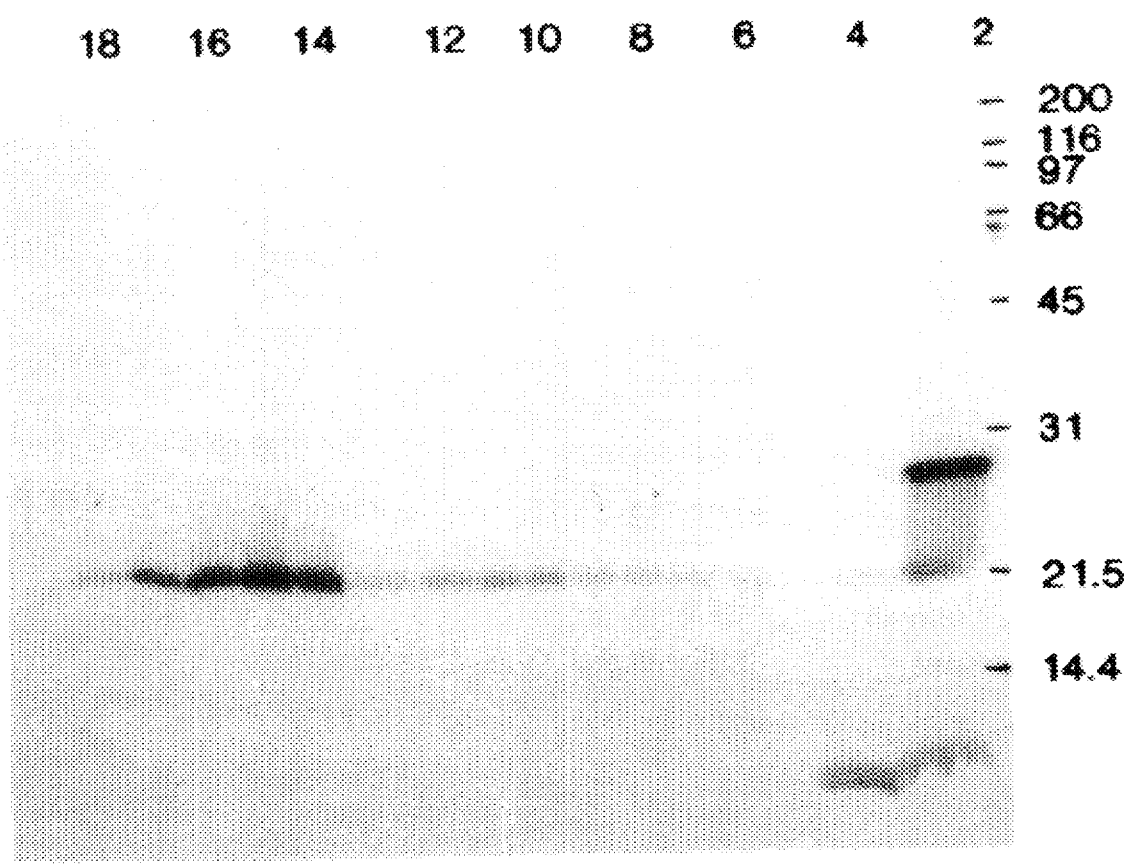
FIG. 5 is a Western blot of different fractions of immunoaffinity purification using E.ACER 10E-2.

FIG. 5 shows a similar blot but from the 10E-2 column binding the Eam20 material.

Lane 3 contained the material that did not bind to the 10C-2A column and was thus the starting material for the 10E-2 adsorbent. It appeared that this fraction did not contain any Eam45 material. The marked band at 29 kD was artefactual and belonged to the Eam20 protein. The artefact was induced by the presence of Triton X114 in the electrophoresis sample.

Lane 4 contained the non-bound fraction of the 10E-2 column, which demonstrated the high efficiency of this MoAb to absorb all Eam20 material.

Although some of the material eluted at pH 2.6 (lanes 10 to 12), the majority was released with 3M KSCN (lanes 14 to 17). These fractions did not contain any non-specifically bound material.

Monoclonals against both Eam45 and Eam20 recognized surface proteins on live merozoites.

The apparent MW of Eam45 as measure on SDS-PAGE was 45–55 kD but for reference to earlier reports it was decided not to change its identification. The MW of Eam45 is accorded about 50 kD herein. On reduced gels Eam45 runs at 55 kD.

All anti-Eam45 sera demonstrated positive reaction around 50 kD and 100 kD if these sera were used to probe back on merozoite blot.

Purification of E. acervulina 100 kD protein from sporozoites

For the purification of the E. acervulina 100 kD protein sporozoites were extracted with TX114 according to the protocol described above. The Eas100 was detected exclusively in the hydrophilic phase. This was subsequently allowed to bind to an immuno-affinity column of Moab E.ACER 5F-2 coupled to CNBr-activated-Sepharose-4B. Binding and elution conditions were as described above.

Figure 6:
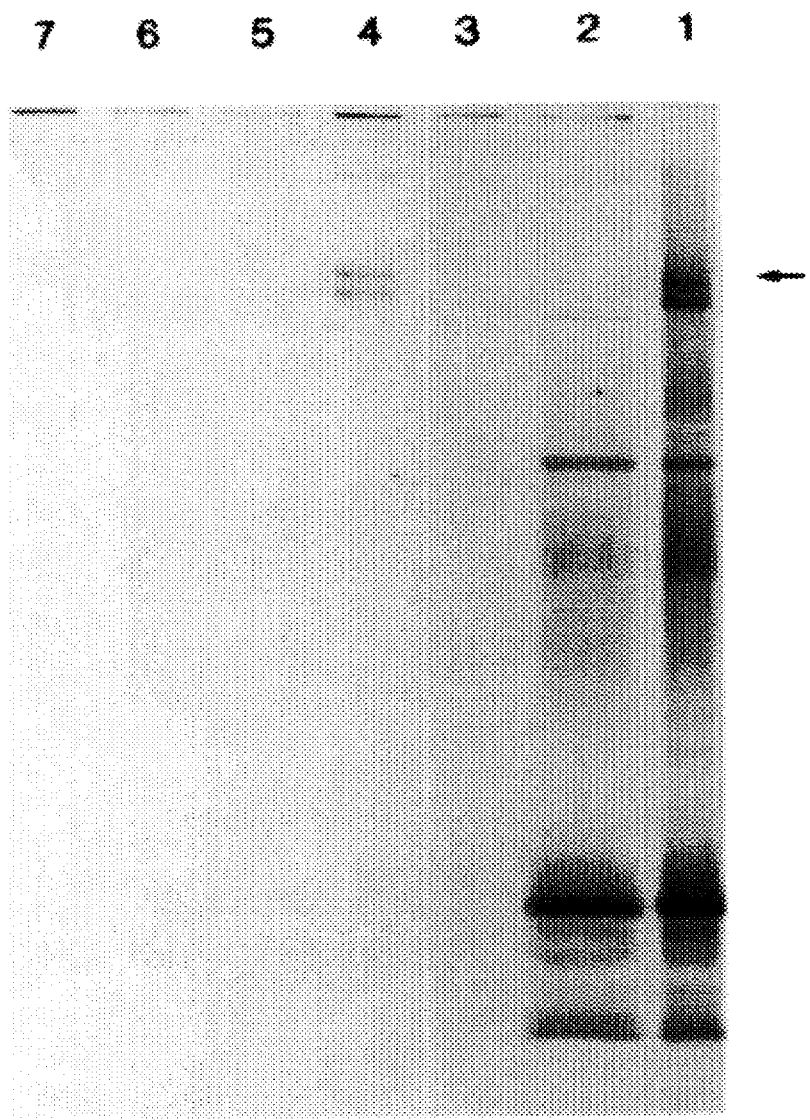
FIG. 6 is a Western blot of different fractions of immunoaffinity purification using E.ACER 5F-2.

The Eas100 eluted as a doublet at acidic pH. The fraction containing Eas100 is shown in FIG. 6 (lane 4). This blot was post-treated with rabbit anti-E.acer sporozoite antibodies.

No other parasite-derived bands were visible in this fraction. The only contaminating band (MW>200 kD) appeared to be caused by IgG leakage from the matrix.

This material was used to raise antibodies in chickens against Eas100.

Antibodies from chicken 323 were used to screen cDNA library derived from 72 hr E.acervulina merozoite mRNA (Example 3).

Ab-selected on the positive clone reacted against the Eas100 as expected and against a protein of similar size in E. acervulina merozoites. Immunoblotted affinity purified Eam100 (using MoAb E.ACER 16B-2B) reacted positively with E.ACER 5F-2, the MoAb that was used to purify the sporozoite equivalent Eas100. Therefore both proteins are related.

Immuno-Affinity Chromatography of Eam200 from Merozoites

Monoclonal antibody E.ACER 11A-2A was coupled to sepharose to bind the Eam200 protein.

Coupling efficiency was over 90%, leakage of MoAb from the column was minimal, however detectable.

The hydrophilic fraction of the TX114 extraction containing Eam200 and Eam100 was allowed to bind to the column according to the protocol as described above for Eam45 and Eam20.

Figure 7:
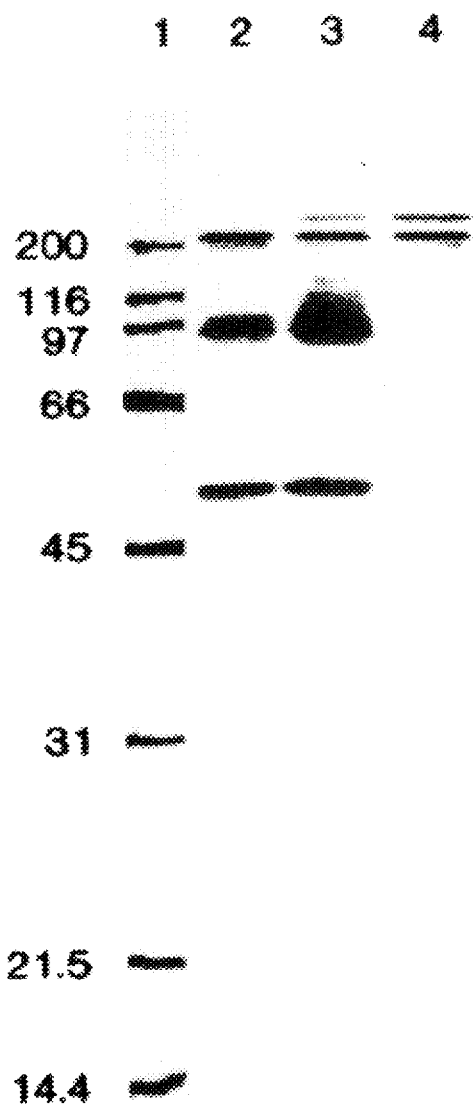
FIG. 7 is a Western blot of different fractions of immunoaffinity purification using E.ACER 11A-2A.

The purified Eam200 was released from the column after acidic elution as is shown in FIG. 7 (lane 4).

Example 3

Preparation of cDNA Library of E. Acervulina Merozoites, Immunological Screening and DNA Sequence Analysis A. Methods Isolation of RNA For the isolation of RNA a pellet of $10^9$ merozoites was resuspended in 0.5 ml $H_2O$. After addition of 0.5 ml solution A (Tris 10 mM, sodium acetate 75 mM, EDTA 2 mM, SDS 1% (pH 7.2)), 1 ml solution B (5M Guanidine-monoisothiocyanaat, EDTA 10 mM, Tris 50 mM (pH 7.5) and 2 g glassbeads (0.5 mm), the suspension was vortexed for 1 min. 4 ml solution B and 0.4 ml β-mercaptoethanol were added and the tubes placed in a waterbath (60° C.) for 15 minutes. After addition of 5 ml phenol the tubes were heated for another 15 minutes at 60° C. and cooled to room temperature (RT). The suspension was mixed by vortexing with 2.5 ml of (0.1M NaAc pH 5.2, 10 mM Tris (pH 7.5), 1 mM EDTA) and 5 ml chloroform-isoamylalcohol (24:1), after which the phases were separated by centrifugation (5 minutes at 6000 rpm). The waterphase was extracted once again with 20 ml phenol-chloroform-isoamylalcohol (25:24:1) by mixing for 10 minutes on a rollerdrum. After centrifugation for 5 minutes at 6000 rpm the nucleic acids were precipitated by addition of 2 volumes ethanol and collected by centrifugation (10 minutes at 6000 rpm). The pellet was washed with 70% ethanol and the poly $A^+$ RNA isolated as described by Maniatis et al. (Maniatis, T. et al., Molecular Cloning, A laboratory Manual, second edition, Cold Spring Harbor Laboratory Press, USA, 1989). Out of $10^9$ merozoites about 1 µg of poly $A^+$ RNA was isolated.

Construction of cDNA Libraries

Poly $A^+$ RNA was converted to cDNA by means of the enzyme MMLV reverse transcriptase. For this purpose 0.5 µg poly $A^+$ mRNA was dissolved in 10 µl $H_2O$, heated for 10 minutes at 65° C. and then quickly cooled on ice. The cDNA synthesis was performed with the cDNA synthesis kit of Pharmacia. In order to obtain bluntended DNA molecules the cDNA was treated with 1 µl Klenow DNA Polymerase (7 U/µl) for 20 minutes at 37° C., followed by an incubation with 1 µl T4 DNA Polymerase (7.5 U/µl) for 10 minutes at 37° C. After extraction with an equal volume of phenol-chloroform-isoamylalcohol (25:24:1) and centrifugation (5 minutes at 13000 rpm, Biofuge), the cDNA was precipitated by the addition of 1 volume $NH_4Ac$ and 4 volumes ethanol. The pellet was washed with 70% ethanol and dissolved in 82 µl $H_2O$. EcoRI adaptors were ligated to the cDNA by addition of 10 µl ligationbuffer (Tris 500 mM (pH 8.0), $MgCl_2$ 100 mM, DTT 100 mM, ATP 100 mM and 50% (w/v) polypropyleneglycol 8000), 5 µl EcoRI adaptor solution (Pharmacia cDNA synthese kit) and 3 µl T4 DNA ligase (7

U/μl) and incubated overnight (O/N) at 12° C. The reaction was stopped by heating (10 minutes at 65° C). The CDNA was phosphorylated by the addition of 10 μl ATP (10 mM) and 2 μl polynucleotide kinase (7 U/μl) and incubation for one hour at 37° C. The CDNA was extracted with 1 volume phenol-chloroform-isoamylalcohol (25:24:1) and purified on a Biogel A-15 m column. The cDNA containing fractions were precipitated by addition of 0.1 volume NaAc (3M NaAc (pH 5.6) and 2 volumes ethanol. The pellet was washed with 70% ethanol and dissolved in 20 μl T10E0.1 (Tris 10 mM (pH 7.6), EDTA 0.1 mM). The cDNA molecules were cloned in λgt10 or λgt11 DNA (according to Huynh et al. in: DNA cloning techniques: A practical approach, 1984).

Screening of Lambda gt11 cDNA Library with Antisera Against Eimeria Proteins.

The lambda gt11 cDNA library was screened with antibodies raised against proteins from Eimeria parasites. Either mouse monoclonal antibodies were used or monospecific rabbit or chicken antisera. Before use the antibodies were diluted in 1×Tris-salt (Tris-HCl 10 mM, NaCl 150 mM, pH 8.0)+0.05% Tween 20+10% Foetal Calf Serum (FCS) and incubated for 2 h at room temperature with the filters. The filters were then washed 4 times, for ten minutes each time, with 50 ml 1×Tris-salt+0.05% Tween 20 for each filter. For the second antibody incubation a conjugate of goat-anti-mouse or goat-anti-rabbit or rabbit-anti-chicken antibodies and alkaline phosphatase was used (diluted 1:7500 in 1×Tris salt +0.05% Tween 20+10% FCS) and incubated for 30 minutes at RT, after which the filters were washed as described above. The colour reaction was carried out in Tris-HCl 100 mM, NaCl 100 mM, MgCl$_2$ 10 mM (pH 9.6) in which 0.33 mg/ml Nitrobluetetrazolium and 0.17 mg/ml 5-Bromo-4-chloro-3-indolyl-phosphate had been dissolved. The reaction was stopped after 30 minutes incubation at room temperature.

Immunopositive clones were purified by two or three additional rounds of plating of isolated plaques and immunological screening as described above.

Characterization of Lambda qt11 cDNA Clones

Phage stocks were prepared and DNA extracted using standard techniques (Maniatis, T. et al., Molecular Cloning, A laboratory Manual, second edition, Cold Spring Harbor Laboratory Press, USA, 1989). After digestion with restriction endonucleases the DNA was analysed by electrophoresis on agarose gels in 89 mM Tris, 89 mM boric acid, 2 mM EDTA, pH 8.3.

Antibody select experiments were performed according to Osaki, L. S. et al. (J. Immunological Methods 89, 213–219, 1986) as a final proof for the identity of the proteins the isolated lambda gt11 cDNA clones are coding for. Phagestocks were diluted to 5×10$^4$ pfu/μl. 1 μl was incubated with 200 μl of cells of E. coli Y1090- and plated. After 2.5 h nitrocellulose filters saturated with IPTG were placed on the plates, after incubation for 5.5 h the filters were turned and the incubation proceeded for another 2 h. The plates with the filters were stored overnight at 4° C., after which the filters were washed with 1×Tris-salt for 20 minutes and blocked with 20% FCS in 1×Tris-salt for 2 h at room temperature. After a Tris-salt wash for 5 minutes at room temperature the filters were dried at the air. Antibody preparations were purified by caprilic acid precipitation and diluted 1:150 in 1×Tris-salt+20% FCS+0.05% NP40. Each filter was incubated with 15 ml of serum for 60 minutes at room temperature. The filters were washed 3× for 10 minutes with 1×Tris-salt+0.05% NP40. The bound IgG was eluted with 5 ml 0.2M Glycine-HCl (pH 2.8) for 1 minute at room temperature, quickly neutralized with 150 μl 2M Tris, 0.2 ml PBS Tween (25×) and 1 ml FCS (all dishes used for the elution steps were first blocked with 1×Tris-salt+10% FCS for 1 h at room temperature). The eluates were used on Western blot strips of Eimeria merozoites or sporozoites for identification of the corresponding proteins.

Screening of Lambda gt10 cDNA Library by Hybridisation

The 200 bp insert from the lambda gt11/Eam 20 clone was labeled with digoxigenin-dUTP by random priming, exactly following the protocol going with the "DNA labeling and detection kit, non-radioactive" from Boehringer, Mannheim (Cat. no. 1093657). Filters containing immobilized DNA from the lambda gt10 E. acervulina cDNA library described above were prepared as described by Maniatis et al. (vide supra) and probed by the freshly denatured (10 min. at 95° C.) labeled E. acervulina cDNA fragment for 16 hours at 42° C. according to the manufacturers instructions. Filters were washed as follows: twice for fifteen minutes with 2×SSC, 0.1% (w/v) SDS (1×SSC is 0.015 mol/l sodium citrate pH 7.0 plus 0.15 mol/l NaCl) at room temperature, twice for fifteen minutes with 1×SSC, 0.1% (w/v) SDS at 60° C., twice for thirty and once for fifteen minutes with 0.1×SSC, 0.1% (w/v) SDS at 60° C. and twice with PBS-tween (7.65 g/l NaCl, 0.91 g/l Na$_2$HPO$_4$.2H$_2$O, 0.21 g/l KH$_2$PO$_4$, 0.05% (v/v) Tween 80, pH 7.3) for 15 minutes at room temperature.

The filters were then reacted with a 1:5000 dilution in PBS-tween of polyclonal sheep anti-digoxigenin Fab fragments, conjugated to alkaline phosphatase, for thirty minutes at room temperature. After washing the filters for four times fifteen minutes with PBS-tween at room temperature and once for fifteen minutes with 0.01M Tris-HCl pH 8.0, 0.15M NaCl, binding of the alkaline phosphatase to the filters was detected upon incubation with a solution of 0.33 g/l Nitroblue tetrazolium and 0.17 g/l 5-bromo-4-chloro-3-indolyl-phosphate in 0.1M Tris-HCl pH 9.6, 0.1M NaCl, 0.01M MgCl$_2$. Positive plaques were purified by two or three additional rounds of plating of isolated plaques and hybridization as described above.

Isolation of Extended DNA Sequences by "Semi-Specific" PCR

Since the initial clones isolated from the lambda gt11 library by immunological screening or from the lambda gt10 library by hybridization analysis did not contain the full-length reading frame for the respective proteins additional DNA sequences were generated by the polymerase chain reaction. Towards this end primary cDNA libraries in lambda gt11 were amplified: 5*10$^4$ pfu were incubated with 600 μl E. coli Y1090$^-$ cells and plated. After overnight incubation the top agarose layer was collected in a tube, 5 ml of phage dilution buffer (Tris (pH 7.6) 10 mM, MgCl$_2$ 10 mM, NaCl 100 mM, gelatine 1 mg/ml) were added and incubated for 16 h at 4° C. The suspension was cleared by centrifugation and the supernatant was used directly for PCR reactions. With modifications the method of Blakely and Carman (BioTechniques 10,53–55 (1991)) was used. To 2.5 μl of the supernatant containing about 10$^{10}$ pfu/μl, 1 μl dNTP stock solution (20 mM of each dNTP), 10 μl of buffer (containing Tris 150 mM (pH 7.6), KCl600 mM, MgCl$_2$ 25 mM), 1 μg of each primer, 3 μl DMSO and 2.5 U of Taq Polymerase (Cetus/Perkin-Elmer) was added in a final reaction mixture of 100 μl. One of each primer set is specific for the Eimeria sequence to be extended, i.e. for either Eam20, Eam45 or Eam100; the second primer of each set is a "general" primer, homologous to the 3'-end of the β-galactosidase gene of lambda gt11 (Lambda gt11 Primer (reverse), 24 MER #1222 (New England Biolabs). PCR fragments were purified by gel-electrophoresis and cloned in the vector of the TA-Cloning kit (Invitrogen) exactly according to the instructions of the manufacturer. Resulting clones were sequenced. To correct for PCR-caused errors in the individual DNA clones at least three independent clones for each extended DNA fragment were sequenced.

DNA Sequence Analysis

The inserts from the λgt10 and λgt11 clones indicated above were subcloned into the pGEM-4Z vector (Promega) for sequencing. Sequencing reactions were carried out by the dideoxy method (Bankier & Barrell, Techniques in the Life Sciences (Biochemistry) 85: Techniques in Nucleic Acids Biochem. 1–34; 1983). Sequencing primers were synthesized on an Applied BioSystems 380B apparatus using the p-cyanoethylphos-phoramadite chemistry.

B. Results

Figure 10:
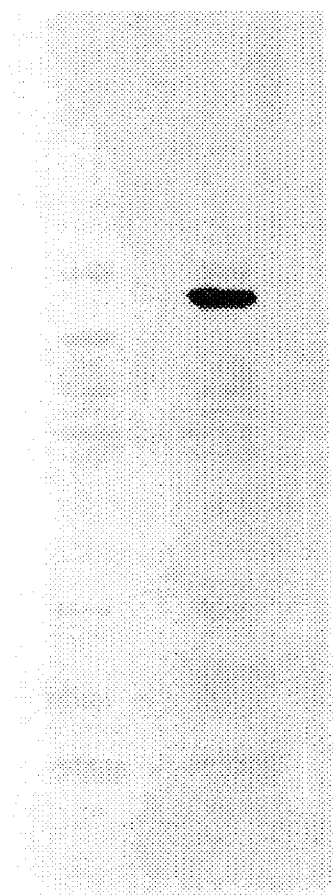
FIG. 10 is a Western blot analysis of lambda gt11/Eam200 expression product.

Clones coding for (part of) the Eam200 reading frame were isolated by using mouse monoclonal antibodies for screening a lambda gt11 cDNA library. One out of every $2.10^5$ independent clones was found to be positive. The reaction of a number of different mouse monoclonal antibodies against Eam200 such as E.ACER 12B-2A, E.ACER 12C-2B and E.ACER 12B-2B, with the clone which was selected for further analysis was considered as sufficient and conclusive evidence for the identity of the reading frame contained within this clone. The reaction of the fusion protein coded for by a lysogenic strain of lambda gt11/Eam 200 with antibody E.ACER 12B-2B is shown in FIG. 10. The sequence of part of Eam200 is shown in SEQ ID No.'s 1 and 2. As can be seen the total insert length is 1491bp, of which 1341bp are coding for protein. Monospecific anti-Eam45 serum from rabbit 5706 (see Example 2) was used for the isolation of clones coding for this protein. Two clones were isolated out of 5.104 plaques screened. The inserts of these clones, which were called Eam45 M1 and Eam45 M3, were 817 and 786 bp respectively. Both inserts were expressed in E. coli: Eam45 M1 coded for a protein of about 13 kD and Eam45 M3 for a 24 kD protein. Both expression products reacted on Western blots with the monospecific rabbit anti-Eam45 serum (data not shown). In antibody-select experiments antibodies eluted from clone M3 were reactive with the merozoite-derived Eam45 protein (FIG. 9); no reaction at all was observed when such experiments were done with clone M1. Extended clones from Eam45 M1 and M3 were prepared by PCR as described in the Methods: for M1 an extended PCR fragment was found of 127 bp and for M3 845 additional bp were found. The total sequence obtained for M1 is therefore 944 bp and for M3 1631 bp. These sequences which have been called Eam45 M1E and Eam45 M3E respectively are shown in SEQ ID NO. 's 4 (M1E) and 5 (M3E). The first ATG in M1E is present at position 82 to 84 and in M3E at position 505 to 507; both ATG's are preceded by in-frame upstream stop codons and therefore most likely represent the true initiation codons. The primary amino acid sequences coded for by Eam45 M1E and M3E are given in SEQ ID NO's 4 (M1E) and 6 (M3E). Monospecific anti-Eam20 from rabbit 5796 (see Example 2) was used for the isolation of clones coding for this protein. All clones isolated from a lambda gt11 expression library had inserts smaller than 200 bp. Therefore, the insert from one of these clones was used as a probe to screen a lambda gt10 library. One out of every 2.105 plaques screened was positive. The longest insert found was 579 bp and has a coding capacity of 11 kD. From this an extended clone was generated using PCR, which contained an additional 221 bp. The total sequence obtained for Eam20 is therefore 800 bp; the clone has been called Eam20E and its sequence is shown in SEQ ID NO. 7. Although the reading frame of Eam20E is completely open from the first nucleotide on, most likely the first ATG (positon 80 to 82 in SEQ ID NO. 7) represents the initiation codon. The protein coding sequence of Eam20E (SEQ ID NO. 8) should thus preferably be read from Met at position 27. For the isolation of clones coding for the Eam100 protein a monospecific serum (323) was used from a chicken which had been immunised with immunoaffinity-purified Eas100. Eas100 was purified by affinity chromatography using immobilized monoclonal antibody E.ACER5F-2 and used to raise antibodies, in chickens as described in Example 2. These antibodies were used to screen a lambda gt11 cDNA library derived from E. acervulina merozoite mRNA. One clone was found to be positive of the 2.105 clones screened. Antibodies selected by this clone from different sera were found to react on Western blots with a 100 kD protein present both in merozoites and sporozoites (see FIG. 8), thus demonstrating that the reading frame of this clone indeed codes for (part of) the 100 kD protein. The insert of this clone was 1259 bp long and has a coding capacity of 34 kD (data not shown). From this an extended clone was generated using PCR, which contained an additional 1116 bp. The total sequence obtained for Eam100 is therefore 2375 bp; it has been called Eam100E and is shown in SEQ ID NO. 9. Its deduced amino acid sequence is shown in SEQ ID NO. 10. In this case the coding sequence may also be read from Met at position 106.

Example 4

Immunization of Chickens with Affinity-Purified Antigens

A. Methods

Starting with $6 \times 10^{10}$ E. acervulina 72 hr merozoites hydrophobic and hydrophilic antigens were separated by TX114 extraction (Example 2). The individual antigens were purified by Immuno-affinity chromatography.

TABLE 1

| Yield of purified E. acervulina merozoite antigens and dose used for immunization. | | |
|---|---|---|
| Antigen | Yield in mg protein | Microgram per dose |
| Eam200 | 0.37 | 5.4 |
| Eam100 | 1.74 | 25 |
| Eam45 | 2.55 | 25 |
| Eam20 | 1.68 | 25 |

Protein concentrations were determined using the Bicinchonic acid assay (Pierce Chemicals) according to the manufacturer's prescription.

Immunization schedule

Purified antigens were mixed with Quil A (Superfos Biosector A/S) so that every dose contained 100 microgram Quil A in a total volume of 0.5 ml. Groups of 20 White Leghorn chickens were kept in isolators from day of hatch until day of priming. The chickens were immunised by three injections of 0.5 ml Quil A/antigen given subcutaneously in the neck with weekly intervals. The antigen dose is given in the Table above.

Challenge

Ten days after the third inoculation chickens were individually dosed with 200–300 freshly sporulated E. acervulina oocysts per os. Oocysts shed were counted from feces-samples taken from days 4 to 7 after infection.

Immunological parameters

Antibody titers

Serum samples were taken prior to every immunization, prior to challenge and 7 days post-challenge. Sera were tested for antibody titers against *E. acervulina* merozoite antigen using an ELISA-test. Hereto $1 \times 10^5$ merozoites in 0.1 ml of 50 mM carbonate/bicarbonate buffer pH 9.6 were coated per well of a microtiter plate by heating overnight at 50° C. Plates were washed, blocked with bovine serum albumin and incubated with different serum dilutions for 1 hr at 37° C., washed several times and subsequently incubated with peroxidase-labelled Rabbit anti-Chicken IgG(H+L) for 1 hr at 37° C. After appropriate washing the positive binding was detected using the Urea-TMB substrate and absorption was measured at 450 nm. Titers are presented as $^2$log(endpoint dilution). Lymphocyte stimulation Prior to challenge peripheral bloodcells were taken from 10 chickens of each group. Peripheral blood leucocytes were isolated by centrifugation of the total blood for 6 min at 64 g at ambient temperature. The buffy coat was removed and residual cells and plasma were remixed and spun again. The white cells harvested from two cycles were counted in a Haemocytometer and concentration adjusted to $1 \times 10^7$ cells per ml in RPMI 1640 (Dutch modification). *E. acervulina* merozoites ($4 \times 10^8$) were suspended in 6.7 ml RPMI 1640 and sonicated using a microtip-equipped Branson sonifier at position 6 for 3×20 seconds with intermediate cooling. This was diluted to meet the concentration used for the stimulation. 96 well round-bottom Tissue culture plates were seeded with 0.05 ml cell suspension, 0.150 ml antigen suspension, cultured for 64 hr at 41° C. under 5% $CO_2$ atmosphere. Subsequently 0.5 microcurie $^3$-H-Thymidine was added per well and 8 hrs later the cells were harvested on a glass-fiber filter (Pharmacia/LKB) using a 96 well Cell Harvester (Skatron Norway). The filters were saturated with scintillation fluid (LKB BetaScint) and counted in a Betaplate 1205 (Pharmacia/LKB Sweden).

B. Results

Immunological parameters

Antibody titers

Table 2 shows the mean pre-challenge titers of the different groups tested in ELISA against A. acervulina merozoite antigen. All antigens induced high Ab-titers which differed a factor of minimum 30 from the controls.

TABLE 2

Mean pre-challenge antibody titers in ELISA against *E. acervulina merozoites*

| Group | Ab-titer $^2$Log (dilution) |
|---|---|
| Eam200 | 16.7 ± 1.1 |
| Eam100 | 14.8 ± 1.4 |
| control | 9.9 ± 1.0 |
| Eam45 | 16.1 ± 1.4 |
| Eam20 | 15.0 ± 1.6 |
| control | 10.1 ± 1.4 |

Lymphocyte stimulation

PBL of all groups were stimulated with three different concentrations of *E. acervulina* merozoite antigens i.e. $5 \times 10^5$, $1 \times 10^6$ and $3 \times 10^6$ sonicated merozoites per well respectively. For every group the optimal concentration was determined. Table 3 shows the mean Dcpm (the cpm of the antigen-stimulated wells minus those of the non-stimulated control). It appeared that all antigens induced a positive T-cell response detectable in the peripheral blood at the time of challenge. In general 6 or 7 out of 10 birds responded versus none in the controls.

TABLE 3

Mean incorporation of $^3$ H-Thymidine after stimulation with merozoite antigen of PBL from groups immunised with different purified *E. acervulina* merozoite antigens expressed as Dcpm.

| Group | $^3$H-thymidine incorporation in Dcpm | responders/non-responders |
|---|---|---|
| Eam200 | 692 | 6/4 |
| Eam100 | 1192 | 8/2 |
| control | 14 | 1/9 |
| Eam45 | 716 | 8/2 |
| Eam20 | 922 | 9/1 |
| control | 6 | 1/9 |

Oocyst production

Table 4 shows the mean number of oocysts shedded per group as percentage of the control, which received only the Quil A adjuvant. Eam200, Eam100, Eam45 and Eam20 reduced the oocyst output.

TABLE 4

Oocyst output in percents from control

| Group | % oocysts (control output = 100%) |
|---|---|
| Eam200/Quil A | 83 |
| Eam100/Quil A | 83 |
| Eam45/Quil A | 62 |
| Eam20/Quil A | 72 |

Legends

Figure 1B:
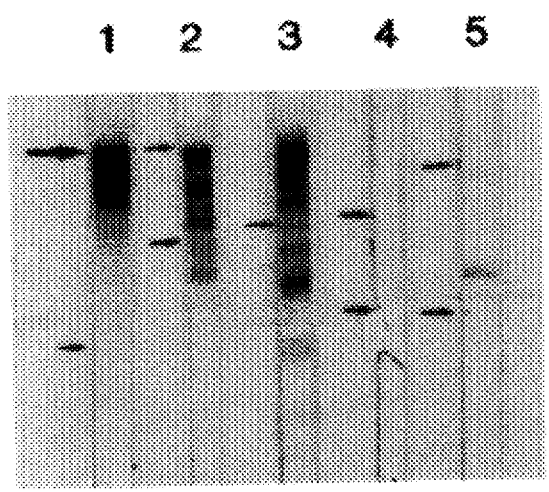

FIG. 1A-1B Recognition of Mabs E.ACER 11A-2A (Panel A) and E.ACER 12B-2B (Panel B) on different Eimeria species and stages. Lanes 1: *E. acervulina* merozoites; non-reduced SDS-PAGE (NR), Lanes 2: *E. acervulina* merozoites; reduced, Lanes 3: *E. acervulina* sporozoites; NR, Lanes 4: *E. tenella* 2nd gen. merozoites; NR, Lanes 5: *E. tenella* sporozoites; NR. Arrows indicate the position of molecular weight markers: beta-galactosidase (MW=116 kD), lower arrow and myosin (MW=200 kD), upper arrow (not indicated in lanes 3).

Figures 2A, 2B:
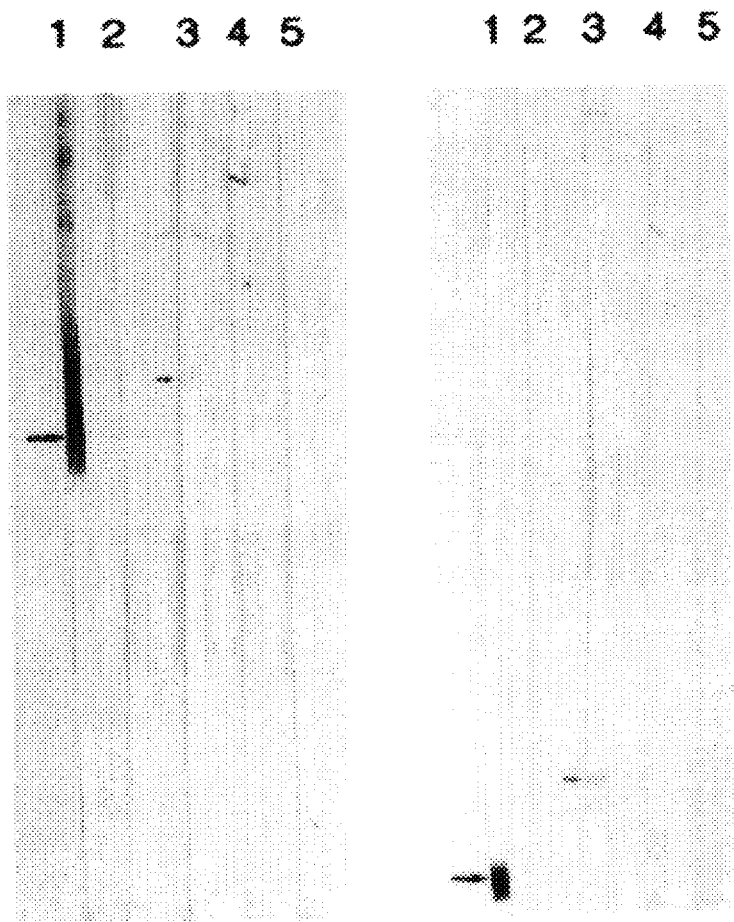
FIG. 2A-2B is a panel of different Eimeria species and stages reacting with monoclonal antibodies E.ACER 10C-2A (Panel A) and E.ACER 10E-2 (Panel B).

FIG. 2A-2b: Recognition of Mabs E.ACER 10C-2A (Panel A) and E.ACER 10E-2 (Panel B) on different Eimeria species and stages. Lanes 1: *E. acervulina* merozoites; non-reduced SDS-PAGE (NR), Lanes 2: *E. acervulina* merozoites; reduced, Lanes 3: *E. acervulina* sporozoites; NR, Lanes 4: *E. tenella* 2nd gen. merozoites; NR, Lanes 5: *E. tenella* sporozoites; NR. Arrows indicate the position of positively recognised bands.

FIG. 3: Western blot (non-reduced PAGE) of different fractions of TX114 extraction of *E. acervulina* merozoites. The blot was probed with a combination of Mabs recognising Eam200 (indicated as "200"), Eam100 ("100"), Eam45 ("50") and Eam20 ("20"). Lane 1: non-solubilised material (concentrated), Lane 2: solubilised total material, Lane 3: hydrophilic fraction (waterphase), Lane 4: sucrose fraction (interphase), Lane 5: hydrophobic fraction (detergent phase).

FIG. 4: Western blot (non-reduced PAGE) of different fractions of immuno-affinity purification usign E.ACER 10C-2A. The blot was probed with K8275 polyclonal rabbitserum. Lane 2: molecular weight markers, Lane 3: TX114 hydrophobic fraction, Lanes 4–10: fractions from washing cycles after binding, Lanes 11–14: acidic elution fractions (pH 2.6), Lanes 15–18: 3M KSCN elution, Lane 19: non-bound fraction.

FIG. 5: Western blot (non-reduced PAGE) of different fractions of immuno-affinity purification using E.ACER 10E-2. The blot was probed with K8275 polyclonal rabbit-serum. Lane 2: molecular weight markers, Lane 3: TX114 hydrophobic fraction after E.ACER 10C-2A column passage, Lane 4: non-bound fraction, Lanes 5–9: fractions from washing cycles after binding, Lanes 10–12: acidic elution fractions (pH 2.6), Lanes 14–18: 3M KSCN elution.

FIG. 6: Western blot (non-reduced PAGE) of different fractions of immuno-affinity purification using E.ACER 5F-2. The blot was probed with polyclonal rabbitserum raised against E. acervulina sporozoites (K802). Lane 1: TX114 hydrophilic fraction of sporozoites, Lane 2: non-bound fraction, Lanes 3–5: acidic elutions fractions (pH 2.6), Lanes 6–7: 3M KSCN elution. Arrow indicates the Eas100 doublet.

FIG. 7: Western blot (non-reduced PAGE) of different fractions of immuno-affinity purification using E.ACER 11A-2A. The blot was probed with a set of monoclonal antibodies reactive with Eam200, Eam100, Eam45 and Eam20. Lane 1: molecular weight markers, Lane 2: TX114 hydrophilic fraction, Lane 3: non-bound fraction, Lane 4: acidic elution fraction (pH 2.6). Just above the Eam200 band a thin IgG band is visible in lanes 3 and 4, caused by leakage of Mab from the column.

Figure 8:
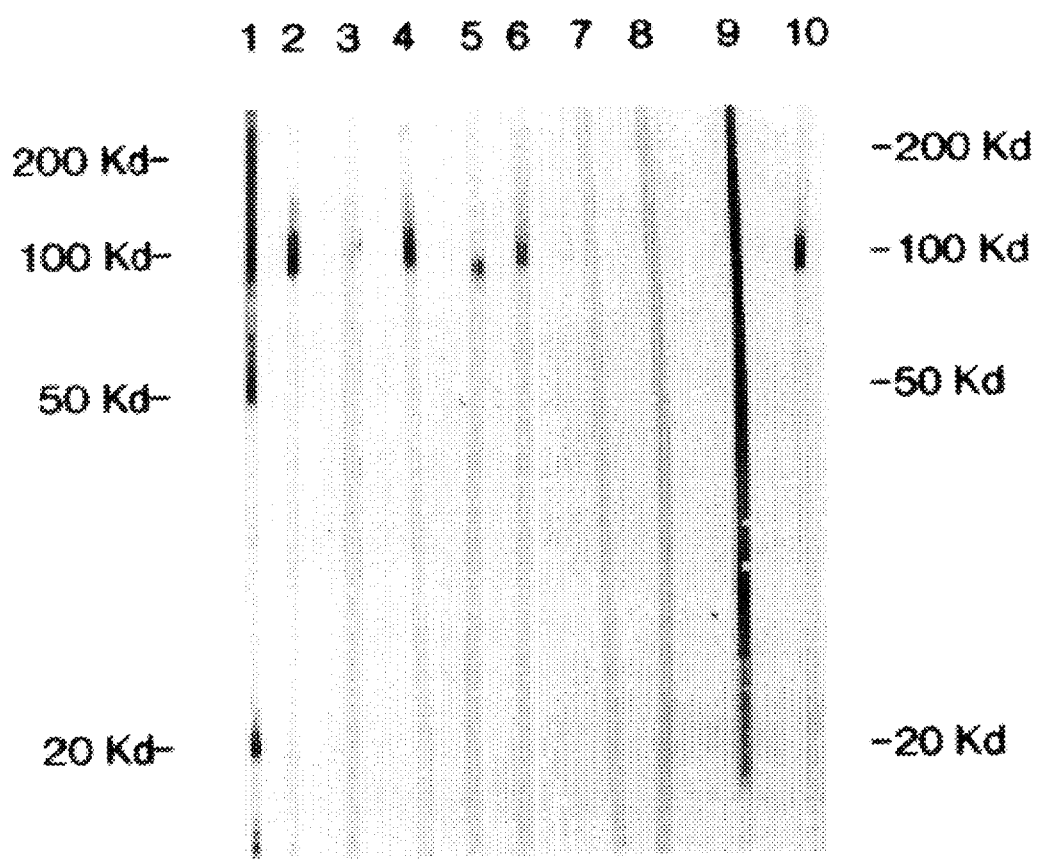
FIG. 8 depicts the reaction of clone Eam100-selected antibodies on Western blot strips of *E. acervulina* proteins.

FIG. 8: Reaction of clone Eam100-selected antibodies on Western blot strips of E. acervulina proteins (non-reduced PAGE). Apart from strip 5 which contains sporozoite proteins from E. acervulina all the other strips contain merozoite proteins. Strips were reacted with:

1. antiserum against total proteins from E. acervulina merozoites (from rabbit K8275)
2. monospecific antiserum against immuno-affinity purified Eam100 (from chicken 323)
3. antibodies selected by clone lambda gt11/Eam100 from chicken 323 antiserum
4. antibodies selected by clone lambda gt11/Eam100 from rabbit K8275 antiserum
5. antibodies selected by clone lambda gt11/Eam100 from rabbit K802 antiserum
6. same as 5
7. antibodies selected by wild type lambda gt11 from chicken 323 antiserum
8. antibodies selected by wild type lambda gt11 from rabbit K802 antiserum
9. antibodies against total sporozoite proteins (from rabbit K802)
10. monoclonal antibody E.ACER 5F-2.

FIG. 9: Reaction of clone Eam45 (M3)-selected antibodies on Western blot strips of E. acervulina proteins (non-reduced PAGE). All strips contain merozoite proteins. They were reacted with:

1. antibodies selected by clone lambda gt11/Eam45 (M3) from rabbit K5706 antiserum
2. antibodies selected by clone lambda gt11/Eam45 (M3) from rabbit K5794 antiserum
3. antibodies selected by clone lambda gt11/Eam45 (M3) from rabbit K5796 antiserum
4. antibodies selected by clone lambda gt11/Eam45 (M3) from rabbit K8275 antiserum
5. monospecific antiserum against immuno-affinity purified Eam45 (from rabbit K5706)
6. antiserum against the TX114 hydrophobic extract from merozoites (from rabbit K5794)
7. monospecific antiserum against immuno-affinity purified Eam45 (from rabbit K5792)
8. antibodies selected by wild type lambda gt11 from rabbit K5706 antiserum
9. antibodies selected by wild type lambda gt11 from rabbit K5794 antiserum
10. antibodies selected by wild type lambda gt11 from rabbit K5796 antiserum
11. antibodies selected by wild type lambda gt11 from rabbit K8275 antiserum
12. monoclonal antibody E.ACER 10C-2A.

FIG. 10. Western blot analysis of lambda gt11/Eam200 expression product. Expression products from a lysogenic strain of lambda gt11/Eam200 were run (reduced) on a SDS-PAGE gel, blotted and probed with monoclonal antibody E.ACER 12B-2B (lane 2). As a control lambda gt11 expression products were run in lane 1.

We claim:

1. An isolated DNA molecule comprising a nucleic acid sequence coding an Eimeria polypeptide having an amino acid sequence selected from the group consisting of: SEQ ID NO:4; SEQ ID NO:6; and fragments of SEQ ID NO:4 and SEQ ID NO:6 that specifically bind with antibody raised to said polypeptide, wherein said DNA molecule is free from other genetic material of Eimeria.

2. The DNA molecule of claim 1, which has a nucleic acid sequence selected from the group consisting of: SEQ ID NO:3; SEQ ID NO:5; and subsequences of SEQ ID NO:3 and SEQ ID NO:5 that code for said fragments.

3. The DNA molecule of claim 1, which codes for the amino acid sequence of SEQ ID NO:4.

4. The DNA molecule of claim 1, which codes for the amino acid sequence of SEQ ID NO:6.

5. The DNA molecule of claim 2, which has the nucleic acid sequence of SEQ ID NO:3.

6. The DNA molecule of claim 2, which has the nucleic acid sequence of SEQ ID NO:5.

7. A recombinant vector, molecule comprising a nucleic acid sequence according to claim 1.

8. A recombinant vector molecule according to claim 7, wherein the nucleic acid sequence is operably linked to expression control sequences.

9. A recombinant vector molecule comprising a nucleic acid sequence according to claim 2.

10. A recombinant vector molecule according to claim 9, wherein the nucleic acid sequence is operable linked to expression control sequences.

11. A recombinant vector virus harboring a heterologous nucleic acid sequence, wherein said sequence is the nucleic acid sequence according to claim 1.

12. The recombinant vector virus according to claim 11, wherein said sequence is the nucleic acid sequence according to claim 2.

13. A host cell transformed with a nucleic acid sequence according to claim 1.

14. A host, cell transformed with a nucleic acid sequence according to claim 2.

15. A host cell transformed with a recombinant vector molecule according to claim 7.

16. A host cell transformed with a recombinant vector molecule according to claim 8.

17. A host cell transformed with a recombinant vector molecule according to claim 9.

18. A host cell transformed with a recombinant vector molecule according to claim 10.

19. A host cell transfected with a recombinant vector virus according to claim 11.

20. A host cell transfected with a recombinant vector virus according to claim 12.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 1491 base pairs
        ( B ) TYPE: nucleic acid
        ( C ) STRANDEDNESS: double
        ( D ) TOPOLOGY: linear ( i i ) MOLECULE TYPE: cDNA to mRNA ( v ) FRAGMENT TYPE: N-terminal ( v i ) ORIGINAL SOURCE:
        ( A ) ORGANISM: Eimeria acervulina
        ( C ) INDIVIDUAL ISOLATE: Merozoites ( v i i ) IMMEDIATE SOURCE:
        ( A ) LIBRARY: Merozoites cDNA lambda gt11

(B) CLONE: Eam200

(ix) FEATURE:
(A) NAME/KEY: CDS
(B) LOCATION: 1..1344

(xi) SEQUENCE DESCRIPTION: SEQ ID NO:1:

| | | | | | | | | | | | | | | | | |
|---|---|---|---|---|---|---|---|---|---|---|---|---|---|---|---|---|
| GAA | TTC | GGG | GGC | ACC | TCC | ACT | ACA | CAC | CTG | ACC | CGG | GAT | GAT | GCA | GTG | 48 |
| Glu | Phe | Gly | Gly | Thr | Ser | Thr | Thr | His | Leu | Thr | Arg | Asp | Asp | Ala | Val | |
| 1 | | | | 5 | | | | | 10 | | | | | 15 | | |
| AAC | ACA | GCG | ATT | GAC | TCG | AAG | CTA | GAC | GAA | TTC | TGC | AAT | CCT | ACA | TCA | 96 |
| Asn | Thr | Ala | Ile | Asp | Ser | Lys | Leu | Asp | Glu | Phe | Cys | Asn | Pro | Thr | Ser | |
| | | | 20 | | | | | 25 | | | | | 30 | | | |
| GAA | CCC | CCT | GAG | GCA | TCG | GGA | AAG | GAG | GAT | TCT | GTC | GAG | GTG | GAG | GAG | 144 |
| Glu | Pro | Pro | Glu | Ala | Ser | Gly | Lys | Glu | Asp | Ser | Val | Glu | Val | Glu | Glu | |
| | | 35 | | | | | 40 | | | | | 45 | | | | |
| ACA | ACA | ACA | ACC | CCA | CCC | AGC | CGT | CCA | TTA | AGG | ATG | CAA | CAT | TTC | GTG | 192 |
| Thr | Thr | Thr | Thr | Pro | Pro | Ser | Arg | Pro | Leu | Arg | Met | Gln | His | Phe | Val | |
| | 50 | | | | | 55 | | | | | 60 | | | | | |
| GAC | GAA | TTT | TGT | CTG | GAG | GAG | GCA | AAG | CGC | GCG | TGT | CAA | AAT | GGG | CTG | 240 |
| Asp | Glu | Phe | Cys | Leu | Glu | Glu | Ala | Lys | Arg | Ala | Cys | Gln | Asn | Gly | Leu | |
| 65 | | | | 70 | | | | | 75 | | | | | 80 | | |
| AGC | GCT | TAC | TGC | GAC | GCC | AGT | GTG | AGC | GCG | CGT | CAC | GAC | GTG | GGA | ACT | 288 |
| Ser | Ala | Tyr | Cys | Asp | Ala | Ser | Val | Ser | Ala | Arg | His | Asp | Val | Gly | Thr | |
| | | | | 85 | | | | | 90 | | | | | 95 | | |
| GAA | CAG | CAG | CGG | ACG | AGG | GAG | TGG | CGC | TGT | TAC | GTG | GAT | GAT | TCC | CTA | 336 |
| Glu | Gln | Gln | Arg | Thr | Arg | Glu | Trp | Arg | Cys | Tyr | Val | Asp | Asp | Ser | Leu | |
| | | 100 | | | | | 105 | | | | | 110 | | | | |
| GAC | TTC | GGC | CTC | TCC | GGC | GAT | GGT | TGT | GTA | GAC | GAC | TGT | GGG | AAT | CTC | 384 |
| Asp | Phe | Gly | Leu | Ser | Gly | Asp | Gly | Cys | Val | Asp | Asp | Cys | Gly | Asn | Leu | |
| | | 115 | | | | | 120 | | | | | 125 | | | | |
| ATC | TCG | TGC | CCT | GGT | GCG | GTA | AAC | GGC | ACC | TCC | ACT | ACA | CAC | CTG | ACC | 432 |
| Ile | Ser | Cys | Pro | Gly | Ala | Val | Asn | Gly | Thr | Ser | Thr | Thr | His | Leu | Thr | |
| | 130 | | | | | 135 | | | | | 140 | | | | | |
| CGG | GAT | GAT | GCA | GTG | AAC | ACA | GCG | ATT | GAC | TCG | AAG | CTA | GAC | GAA | TTC | 480 |
| Arg | Asp | Asp | Ala | Val | Asn | Thr | Ala | Ile | Asp | Ser | Lys | Leu | Asp | Glu | Phe | |
| 145 | | | | 150 | | | | | 155 | | | | | 160 | | |
| TGC | AAT | CCT | ACA | TCA | GAA | CCC | CCT | GAG | GCA | TCG | GAG | AAG | AAG | GAA | TCC | 528 |
| Cys | Asn | Pro | Thr | Ser | Glu | Pro | Pro | Glu | Ala | Ser | Glu | Lys | Lys | Glu | Ser | |
| | | | | 165 | | | | | 170 | | | | | 175 | | |
| GTC | GAG | GTG | CCA | GAG | ACA | ACA | GCG | CTG | CCT | TCG | AAC | CCC | CCA | TCA | AAT | 576 |
| Val | Glu | Val | Pro | Glu | Thr | Thr | Ala | Leu | Pro | Ser | Asn | Pro | Pro | Ser | Asn | |
| | | | 180 | | | | | 185 | | | | | 190 | | | |
| CTA | CAA | GCT | TTG | GTG | GAT | GGG | CTT | TGT | GCT | GAG | GAG | GGG | AGA | AAA | GCG | 624 |
| Leu | Gln | Ala | Leu | Val | Asp | Gly | Leu | Cys | Ala | Glu | Glu | Gly | Arg | Lys | Ala | |
| | | 195 | | | | | 200 | | | | | 205 | | | | |
| TGC | GGA | CAA | GGG | CTG | CAA | GCC | TAC | TGC | GAC | ACT | GAT | ATG | TTC | GCA | CGC | 672 |
| Cys | Gly | Gln | Gly | Leu | Gln | Ala | Tyr | Cys | Asp | Thr | Asp | Met | Phe | Ala | Arg | |
| | 210 | | | | | 215 | | | | | 220 | | | | | |
| CAC | GAC | GTC | GGA | ACT | GGG | AGT | CAG | AGG | AAC | AGG | GAG | TGG | CGC | TGC | TAT | 720 |
| His | Asp | Val | Gly | Thr | Gly | Ser | Gln | Arg | Asn | Arg | Glu | Trp | Arg | Cys | Tyr | |
| 225 | | | | 230 | | | | | 235 | | | | | 240 | | |
| GCA | CGA | GTG | TCG | TTG | GAC | TTC | GGC | ATA | TCC | GGC | GAT | GGT | TGT | GTA | GAC | 768 |
| Ala | Arg | Val | Ser | Leu | Asp | Phe | Gly | Ile | Ser | Gly | Asp | Gly | Cys | Val | Asp | |
| | | | | 245 | | | | | 250 | | | | | 255 | | |
| GAC | TGT | GGG | AAT | CTC | ACA | TCT | TGC | CTT | GGT | GCG | GTA | AAC | GGT | TCC | TCG | 816 |
| Asp | Cys | Gly | Asn | Leu | Thr | Ser | Cys | Leu | Gly | Ala | Val | Asn | Gly | Ser | Ser | |
| | | | 260 | | | | | 265 | | | | | 270 | | | |
| ACT | ACG | CAT | CTC | TCA | CGG | GGA | GAA | CGT | ATT | CAA | AAA | CTT | ATT | GAC | ACA | 864 |
| Thr | Thr | His | Leu | Ser | Arg | Gly | Glu | Arg | Ile | Gln | Lys | Leu | Ile | Asp | Thr | |
| | | 275 | | | | | 280 | | | | | 285 | | | | |

| | | | | | | | | | | | | | | | | |
|---|---|---|---|---|---|---|---|---|---|---|---|---|---|---|---|---|
| GAG | AAA | GCT | GGA | CGG | TGC | ACA | CCA | GAG | GAG | GGC | GAA | GAG | GCA | GGT | GGG | 912 |
| Glu | Lys 290 | Ala | Gly | Arg | Cys | Thr 295 | Pro | Glu | Glu | Gly 300 | Glu | Glu | Ala | Gly | Gly | |
| AGC | CCT | GCT | CCA | GCC | CCA | GTG | CCA | GAA | CTT | CCT | GCA | GGA | GTA | CCG | GCG | 960 |
| Ser 305 | Pro | Ala | Pro | Ala | Pro 310 | Val | Pro | Glu | Leu | Pro 315 | Ala | Gly | Val | Pro | Ala 320 | |
| TCT | GAG | GTG | TCG | GAC | AAG | GGC | CTG | AAG | GTT | CCT | CCA | AGG | GTC | CCA | GGT | 1008 |
| Ser | Glu | Val | Ser | Asp 325 | Lys | Gly | Leu | Lys | Val 330 | Pro | Pro | Arg | Val | Pro 335 | Gly | |
| GGT | GGA | GCT | TTA | CAA | GAA | ATG | GCT | GAC | GTC | AGG | TGC | ATG | GTG | TTC | TTT | 1056 |
| Gly | Gly | Ala | Leu 340 | Gln | Glu | Met | Ala | Asp 345 | Val | Arg | Cys | Met | Val 350 | Phe | Phe | |
| GCA | AAG | CAG | TGT | GTA | ACT | GAC | GAA | AGC | ATG | TGC | CAA | TAC | GCC | GTG | GCC | 1104 |
| Ala | Lys | Gln 355 | Cys | Val | Thr | Asp | Glu 360 | Ser | Met | Cys | Gln | Tyr 365 | Ala | Val | Ala | |
| CGC | AAA | ATT | GAC | TCC | ACG | TGG | AAG | TGT | TAC | CCG | TAT | GGT | GCA | GTT | GAT | 1152 |
| Arg | Lys 370 | Ile | Asp | Ser | Thr | Trp 375 | Lys | Cys | Tyr | Pro | Tyr 380 | Gly | Ala | Val | Asp | |
| GAC | TCG | CAG | TCA | GGT | GAT | GCT | TGT | ACA | GAC | GAC | TGT | GGC | AAT | GCA | ATA | 1200 |
| Asp 385 | Ser | Gln | Ser | Gly | Asp 390 | Ala | Cys | Thr | Asp | Asp 395 | Cys | Gly | Asn | Ala | Ile 400 | |
| AAC | TGT | CCG | GGT | ATT | CCG | AAG | AAT | GGA | GAT | GCC | GAC | GGC | ATG | AGA | ATT | 1248 |
| Asn | Cys | Pro | Gly | Ile 405 | Pro | Lys | Asn | Gly | Asp 410 | Ala | Asp | Gly | Met | Arg 415 | Ile | |
| CCA | GCC | CTC | GAT | CAC | CTG | TTC | GAA | GAG | TTG | AAG | AGC | GCC | ACC | TGC | AAG | 1296 |
| Pro | Ala | Leu | Asp 420 | His | Leu | Phe | Glu | Glu 425 | Leu | Lys | Ser | Ala | Thr 430 | Cys | Lys | |
| ATG | AGC | AAA | CAG | CAA | GAG | CTC | AAG | AAA | GTT | CAC | GTG | CAT | CGG | CAA | | 1341 |
| Met | Ser | Lys 435 | Gln | Gln | Glu | Leu | Lys 440 | Lys | Val | His | Val | His 445 | Arg | Gln | | |

| | |
|---|---|
| TGACGAGAGG | 1351 |
| GTGTGCTGAC TGGACGACGT GGGTTGCGAG GCCAAACTCA ATGCTAAGCA AGTGAATGAC | 1411 |
| AATATAAGTA TTCTGCTGCC GGAAGTACTG AAGTCTTCCC TTATCCAATG CAAAGCAAGG | 1471 |
| CTATCCATGG CCTGGCAGGG | 1491 |

( 2 ) INFORMATION FOR SEQ ID NO:2:

( i ) SEQUENCE CHARACTERISTICS:
        ( A ) LENGTH: 447 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Glu 1 | Phe | Gly | Gly | Thr 5 | Ser | Thr | Thr | His | Leu 10 | Thr | Arg | Asp | Asp | Ala 15 | Val |
| Asn | Thr | Ala | Ile 20 | Asp | Ser | Lys | Leu | Asp 25 | Glu | Phe | Cys | Asn | Pro 30 | Thr | Ser |
| Glu | Pro | Pro 35 | Glu | Ala | Ser | Gly | Lys 40 | Glu | Asp | Ser | Val | Glu 45 | Val | Glu | Glu |
| Thr | Thr 50 | Thr | Thr | Pro | Pro | Ser 55 | Arg | Pro | Leu | Arg | Met 60 | Gln | His | Phe | Val |
| Asp 65 | Glu | Phe | Cys | Leu | Glu 70 | Glu | Ala | Lys | Arg | Ala 75 | Cys | Gln | Asn | Gly | Leu 80 |
| Ser | Ala | Tyr | Cys | Asp 85 | Ala | Ser | Val | Ser | Ala 90 | Arg | His | Asp | Val | Gly 95 | Thr |
| Glu | Gln | Gln | Arg 100 | Thr | Arg | Glu | Trp | Arg 105 | Cys | Tyr | Val | Asp | Asp 110 | Ser | Leu |

| | | | | | | | | | | | | | |
|---|---|---|---|---|---|---|---|---|---|---|---|---|---|
| Asp | Phe | Gly<br>115 | Leu | Ser | Gly | Asp<br>120 | Gly | Cys | Val | Asp | Cys<br>125 | Gly | Asn | Leu |
| Ile | Ser | Cys<br>130 | Pro | Gly | Ala | Val<br>135 | Asn | Gly | Thr | Ser | Thr<br>140 | Thr | His | Leu | Thr |
| Arg<br>145 | Asp | Asp | Ala | Val | Asn<br>150 | Thr | Ala | Ile | Asp | Ser<br>155 | Lys | Leu | Asp | Glu | Phe<br>160 |
| Cys | Asn | Pro | Thr | Ser<br>165 | Glu | Pro | Pro | Glu | Ala<br>170 | Ser | Glu | Lys | Lys | Glu<br>175 | Ser |
| Val | Glu | Val | Pro<br>180 | Glu | Thr | Thr | Ala | Leu<br>185 | Pro | Ser | Asn | Pro<br>190 | Ser | Asn |
| Leu | Gln | Ala<br>195 | Leu | Val | Asp | Gly | Leu<br>200 | Cys | Ala | Glu | Gly<br>205 | Arg | Lys | Ala |
| Cys | Gly<br>210 | Gln | Gly | Leu | Gln | Ala<br>215 | Tyr | Cys | Asp | Thr | Asp<br>220 | Met | Phe | Ala | Arg |
| His<br>225 | Asp | Val | Gly | Thr | Gly<br>230 | Ser | Gln | Arg | Asn | Arg<br>235 | Glu | Trp | Arg | Cys | Tyr<br>240 |
| Ala | Arg | Val | Ser | Leu<br>245 | Asp | Phe | Gly | Ile | Ser<br>250 | Gly | Asp | Gly | Cys<br>255 | Val | Asp |
| Asp | Cys | Gly | Asn<br>260 | Leu | Thr | Ser | Cys | Leu<br>265 | Gly | Ala | Val | Asn<br>270 | Gly | Ser | Ser |
| Thr | Thr | His<br>275 | Leu | Ser | Arg | Gly | Glu<br>280 | Arg | Ile | Gln | Lys | Leu<br>285 | Ile | Asp | Thr |
| Glu | Lys<br>290 | Ala | Gly | Arg | Cys | Thr<br>295 | Pro | Glu | Glu | Gly | Glu<br>300 | Glu | Ala | Gly | Gly |
| Ser<br>305 | Pro | Ala | Pro | Ala | Pro<br>310 | Val | Pro | Glu | Leu | Pro<br>315 | Ala | Gly | Val | Pro | Ala<br>320 |
| Ser | Glu | Val | Ser | Asp<br>325 | Lys | Gly | Leu | Lys | Val<br>330 | Pro | Pro | Arg | Val | Pro<br>335 | Gly |
| Gly | Gly | Ala | Leu<br>340 | Gln | Glu | Met | Ala | Asp<br>345 | Val | Arg | Cys | Met | Val<br>350 | Phe | Phe |
| Ala | Lys | Gln<br>355 | Cys | Val | Thr | Asp | Glu<br>360 | Ser | Met | Cys | Gln | Tyr<br>365 | Ala | Val | Ala |
| Arg | Lys<br>370 | Ile | Asp | Ser | Thr | Trp<br>375 | Lys | Cys | Tyr | Pro | Tyr<br>380 | Gly | Ala | Val | Asp |
| Asp<br>385 | Ser | Gln | Ser | Gly | Asp<br>390 | Ala | Cys | Thr | Asp | Asp<br>395 | Cys | Gly | Asn | Ala | Ile<br>400 |
| Asn | Cys | Pro | Gly | Ile<br>405 | Pro | Lys | Asn | Gly | Asp<br>410 | Ala | Asp | Gly | Met | Arg<br>415 | Ile |
| Pro | Ala | Leu | Asp<br>420 | His | Leu | Phe | Glu | Glu<br>425 | Leu | Lys | Ser | Ala | Thr<br>430 | Cys | Lys |
| Met | Ser | Lys<br>435 | Gln | Gln | Glu | Leu | Lys<br>440 | Lys | Val | His | Val | His<br>445 | Arg | Gln |

( 2 ) INFORMATION FOR SEQ ID NO:3:

( i ) SEQUENCE CHARACTERISTICS:
    ( A ) LENGTH: 944 base pairs
    ( B ) TYPE: nucleic acid
    ( C ) STRANDEDNESS: double
    ( D ) TOPOLOGY: linear ( i i ) MOLECULE TYPE: cDNA to mRNA ( v ) FRAGMENT TYPE: N-terminal ( v i ) ORIGINAL SOURCE:
    ( A ) ORGANISM: Eimeria acervulina (vii) IMMEDIATE SOURCE:
  (B) CLONE: Eam45 M1E (ix) FEATURE:
  (A) NAME/KEY: CDS
  (B) LOCATION: 82..489

(xi) SEQUENCE DESCRIPTION: SEQ ID NO:3:

```
TTTTTTTTT  TTTTGCTCTC  CATTTTCCCA  ACAATATTTC  TCTGTTTCTC  GTCTTAGGTC                    60

CGCCTAACCA ACATTTAGGA A ATG AGT TCG AAT CCA CGA CTC CGG GAA GCC                         111
                        Met Ser Ser Asn Pro Arg Leu Arg Glu Ala
                         1               5                   10

TTT GCC CTT TTC GAC AGG GAT GGA GAC GGA GAG TTG ACT GCC AGC GAG                         159
Phe Ala Leu Phe Asp Arg Asp Gly Asp Gly Glu Leu Thr Ala Ser Glu
                 15              20                  25

GCT CTA TTG GCT ATC CGT TCT ACG GGG GTT ATT GTG GCT GCC GAG GAG                         207
Ala Leu Leu Ala Ile Arg Ser Thr Gly Val Ile Val Ala Ala Glu Glu
             30              35                  40

GCA AGC AGC CTG CCG ACC ACC ATG AAC TGG GAG CAG TTT GAG AGT TGG                         255
Ala Ser Ser Leu Pro Thr Thr Met Asn Trp Glu Gln Phe Glu Ser Trp
             45              50                  55

GTC AAC AAG AAA CTG AGC AGC AGC AAC CCG GAG GCG GAC TTA ATC AAG                         303
Val Asn Lys Lys Leu Ser Ser Ser Asn Pro Glu Ala Asp Leu Ile Lys
         60              65                  70

TCC TTT AAA GTA TTT GAC ACA AAG GGG GAC GGC ACT CTC TCG ACA GAC                         351
Ser Phe Lys Val Phe Asp Thr Lys Gly Asp Gly Thr Leu Ser Thr Asp
 75              80                  85                      90

GAA CTT ATG CAA GTT ATA AAG ACC TTA GGA GAT CTG CTG ACG GAC GAA                         399
Glu Leu Met Gln Val Ile Lys Thr Leu Gly Asp Leu Leu Thr Asp Glu
                 95              100                 105

GAG GTT GAG CGT ATG GTT AAT GAC GCA GAC CCA AGC AAA ACA GGG CGA                         447
Glu Val Glu Arg Met Val Asn Asp Ala Asp Pro Ser Lys Thr Gly Arg
             110             115                 120

ATT AAA TAT GCC GAT TTT GTA AAG TAC CTC TTG AGC AAC TGACTTCATG                          496
Ile Lys Tyr Ala Asp Phe Val Lys Tyr Leu Leu Ser Asn
             125             130                 135

GGTTCATGCA  GCACCCCACC  ACAGCAGTTA  AAGCGCTCCT  GCTATACTCA  CGTACATGTT                   556
GTTCGTGAAC  GTATGCATGG  CTAGGGTTAT  TTGAACCGCA  CGGGTTCATT  TTGTGCGTTT                   616
AGTGGAGCCT  CTGCCCATCG  GGTGCTTCCT  CACCTAGCTC  TCACAGCAGA  GGGCCGAGCG                   676
CAGGTGTTGC  TTTGCCATGG  TGCATGTGGG  AGTTGCAATC  TTTAACCTGC  GTGCCGCCTG                   736
TGTGTTGCTC  GCTGCACAGC  TGGGGCAGTA  TTGCATGCAC  CACATGCATT  ACGATGGACA                   796
AAAGACGGGG  AGGGGAGCTA  TGCCTTTCGG  TGCTTCTGCC  GAGAAAGCGA  GCAGCATGCA                   856
TGCATGTGTG  CAACATACAT  GCGCCAATGT  GAGCTATACA  ACCCCTCCAG  GCCTTTTTTA                   916
TGTGAACGAT  TTGGAACCGA  CAAGTCAG                                                        944
```

(2) INFORMATION FOR SEQ ID NO:4:

(i) SEQUENCE CHARACTERISTICS:
    (A) LENGTH: 135 amino acids
    (B) TYPE: amino acid
    (D) TOPOLOGY: linear (ii) MOLECULE TYPE: protein (xi) SEQUENCE DESCRIPTION: SEQ ID NO:4:

```
Met Ser Ser Asn Pro Arg Leu Arg Glu Ala Phe Ala Leu Phe Asp Arg
 1               5                   10                  15

Asp Gly Asp Gly Glu Leu Thr Ala Ser Glu Ala Leu Leu Ala Ile Arg
             20              25                  30
```

| | | | | | | | | | | | | | | |
|---|---|---|---|---|---|---|---|---|---|---|---|---|---|---|
| Ser | Thr | Gly | Val | Ile | Val | Ala | Ala | Glu | Glu | Ala | Ser | Ser | Leu | Pro | Thr |
| | | 35 | | | | | 40 | | | | 45 | | | | |
| Thr | Met | Asn | Trp | Glu | Gln | Phe | Glu | Ser | Trp | Val | Asn | Lys | Lys | Leu | Ser |
| | 50 | | | | | 55 | | | | | 60 | | | | |
| Ser | Ser | Asn | Pro | Glu | Ala | Asp | Leu | Ile | Lys | Ser | Phe | Lys | Val | Phe | Asp |
| 65 | | | | | 70 | | | | 75 | | | | | | 80 |
| Thr | Lys | Gly | Asp | Gly | Thr | Leu | Ser | Thr | Asp | Glu | Leu | Met | Gln | Val | Ile |
| | | | | 85 | | | | | 90 | | | | | 95 | |
| Lys | Thr | Leu | Gly | Asp | Leu | Leu | Thr | Asp | Glu | Glu | Val | Glu | Arg | Met | Val |
| | | | 100 | | | | | 105 | | | | | 110 | | |
| Asn | Asp | Ala | Asp | Pro | Ser | Lys | Thr | Gly | Arg | Ile | Lys | Tyr | Ala | Asp | Phe |
| | | 115 | | | | | 120 | | | | | 125 | | | |
| Val | Lys | Tyr | Leu | Leu | Ser | Asn | | | | | | | | | |
| 130 | | | | | | 135 | | | | | | | | | |

(2) INFORMATION FOR SEQ ID NO:5:

(i) SEQUENCE CHARACTERISTICS:
        (A) LENGTH: 1631 base pairs
        (B) TYPE: nucleic acid
        (C) STRANDEDNESS: double
        (D) TOPOLOGY: linear (ii) MOLECULE TYPE: cDNA to mRNA (vii) IMMEDIATE SOURCE:
        (B) CLONE: Eam45 M3E (ix) FEATURE:
        (A) NAME/KEY: CDS
        (B) LOCATION: 505..1494

(xi) SEQUENCE DESCRIPTION: SEQ ID NO:5:

| | | | | | |
|---|---|---|---|---|---|
| CAACACATTT | GGGGGAGCTC | AGCTAAAGTA | TTTGTCGTTT | CAGCCACAAG | GCCAACTCCC | 60 |
| TCTTCCTCAG | GGACCAAAAT | CAGCTGTGAT | GAAGCCCTCA | GCGAGTGGAA | GACAGGGTTT | 120 |
| GCAAATTTCG | AGGGCCAAGA | TCCTCCGGCA | TACTCAGACG | CCACCTTGGT | ATATGCAAAC | 180 |
| CCAAATTCGG | TAGGCCTTGT | CAGCCTGCTG | AGCGCGACGC | AGCAGACCAT | TTACTGCGGA | 240 |
| ACTACAGATA | CGTGTGGAGA | TGATACCCTC | GTTTGCTACT | ACAAGCCCTC | TGGCATAGAG | 300 |
| GAGGAAACGG | TTCCTGTGAG | CGAAGATCTG | TGGCACAAGT | GCAGGAATC | CCACAAGGTG | 360 |
| AAGCCCGCAC | TGGCAGCTGA | CGATGCGGGC | TCCCTAGCTG | CGTGACAGCA | GTCAATGCTG | 420 |
| CTCGGGGTGC | CGGAGTCTGG | AACTTGCGGG | CTTCACAAAA | GGCTCTAACT | TGGAGGCTGG | 480 |

| | | | | | | | | |
|---|---|---|---|---|---|---|---|---|
| CGCAAAGAAG | CTGTATGGAT | TGAC | ATG CGA | ACG ATA | GAT ACC | ATG ACA | GTC | 531 |
| | | | Met Arg | Thr Ile | Asp Thr | Met Thr | Val | |
| | | | 1 | | 5 | | | |

| | | | | | | | | | | | | |
|---|---|---|---|---|---|---|---|---|---|---|---|---|
| GAC | CCA | ACG | GCG | GCA | CGA | GGC | CAC | ACT | ATC | ATC | TAC | GCC | ACA | AAA | GAA | 579 |
| Asp | Pro | Thr | Ala | Ala | Arg | Gly | His | Thr | Ile | Ile | Tyr | Ala | Thr | Lys | Glu | |
| 10 | | | | | 15 | | | | | 20 | | | | | 25 | |

| | | | | | | | | | | | | |
|---|---|---|---|---|---|---|---|---|---|---|---|---|
| GGG | GAC | ACT | CCT | CCA | ACG | GCA | GAA | GAA | GCC | GTT | GAG | CAA | TGG | AAA | AAA | 627 |
| Gly | Asp | Thr | Pro | Pro | Thr | Ala | Glu | Glu | Ala | Val | Glu | Gln | Trp | Lys | Lys | |
| | | | | 30 | | | | | 35 | | | | | 40 | | |

| | | | | | | | | | | | | |
|---|---|---|---|---|---|---|---|---|---|---|---|---|
| GGG | GCA | GCA | CGG | CTC | GGC | ACC | GGC | GTC | CTG | CCT | GCC | TTC | ACG | AAG | AAG | 675 |
| Gly | Ala | Ala | Arg | Leu | Gly | Thr | Gly | Val | Leu | Pro | Ala | Phe | Thr | Lys | Lys | |
| | | | | 45 | | | | | 50 | | | | | 55 | | |

| | | | | | | | | | | | | |
|---|---|---|---|---|---|---|---|---|---|---|---|---|
| TCG | AAA | GCA | GCC | GAC | GGC | GAG | ATC | TAC | TAT | GAC | AGC | GCA | GTA | GCC | GGT | 723 |
| Ser | Lys | Ala | Ala | Asp | Gly | Glu | Ile | Tyr | Tyr | Asp | Ser | Ala | Val | Ala | Gly | |
| | | | 60 | | | | | 65 | | | | | 70 | | | |

| | | | | | | | | | | | | |
|---|---|---|---|---|---|---|---|---|---|---|---|---|
| TTC | GTC | TCC | ATT | ATG | ACT | GAT | AAT | ACC | CGC | GAA | ACG | GCA | TGC | TAC | AAA | 771 |
| Phe | Val | Ser | Ile | Met | Thr | Asp | Asn | Thr | Arg | Glu | Thr | Ala | Cys | Tyr | Lys | |

|   | 75 |   |   |   | 80 |   |   |   | 85 |   |   |   |   |   |   |
|---|---|---|---|---|---|---|---|---|---|---|---|---|---|---|---|

```
         75                          80                           85
GCT ACA GGT TGC ACT AAC GCC GCA CTC ATC TGC TTA CTT AAA GGG CCA                819
Ala Thr Gly Cys Thr Asn Ala Ala Leu Ile Cys Leu Leu Lys Gly Pro
 90              95                 100                     105

ACT CTG GAG GAA AAC CAA AAG CCC ATC ACC GAC GAA ACA TGG AAA AAG                867
Thr Leu Glu Glu Asn Gln Lys Pro Ile Thr Asp Glu Thr Trp Lys Lys
                    110                 115                 120

GTC TTG GAT GTC TAC GGA GAA AAG ATG GAT TTC AAA GAA CGT GAG GAG                915
Val Leu Asp Val Tyr Gly Glu Lys Met Asp Phe Lys Glu Arg Glu Glu
                125                 130                 135

GGA GAA AGC TGC CTC ACG GAG ATA AAT GAT TTC CGC GCC CAA GAT GGC                963
Gly Glu Ser Cys Leu Thr Glu Ile Asn Asp Phe Arg Ala Gln Asp Gly
            140                 145                 150

CTC GCT CTG CCA CCG TTC GCT GCC GCG ACG GAC TTA CAT GGT GCG AAA               1011
Leu Ala Leu Pro Pro Phe Ala Ala Ala Thr Asp Leu His Gly Ala Lys
    155                 160                 165

CCG AAG GCT TCC GAA TTG ATT GGG AAA GGC TTG ACG TGC GAG GCC CTC               1059
Pro Lys Ala Ser Glu Leu Ile Gly Lys Gly Leu Thr Cys Glu Ala Leu
170                 175                 180                 185

AAG TCT GGG AAT GCC CCC ATC TTG TTT ACC GAC CAA GAA ATA AGC CTG               1107
Lys Ser Gly Asn Ala Pro Ile Leu Phe Thr Asp Gln Glu Ile Ser Leu
                190                 195                 200

ATG TAC TAC ATG GGT GAA ACT GCC ACT TGC TCT TTA GCC GTC AGA GAA               1155
Met Tyr Tyr Met Gly Glu Thr Ala Thr Cys Ser Leu Ala Val Arg Glu
                205                 210                 215

TGG AAA AAT GGC ATT GAC TTG TTC AGC GAC TTC ACC ATC CCT CCA AAG               1203
Trp Lys Asn Gly Ile Asp Leu Phe Ser Asp Phe Thr Ile Pro Pro Lys
            220                 225                 230

TAC ACT TCA ACC GAA GAA GTT TAC AAG AAG GGA GCA GCA ACA AAC TTT               1251
Tyr Thr Ser Thr Glu Glu Val Tyr Lys Lys Gly Ala Ala Thr Asn Phe
    235                 240                 245

ATC TCC CTC GTC AGC GAA GGA ACT GAT ACC AAA ATA AAA TGC TAC ACC               1299
Ile Ser Leu Val Ser Glu Gly Thr Asp Thr Lys Ile Lys Cys Tyr Thr
250                 255                 260                 265

GTG ACA GGC TGC AGC GAA CCA GGA TTG CTT TGC CTG CTG CAA CCT CCT               1347
Val Thr Gly Cys Ser Glu Pro Gly Leu Leu Cys Leu Leu Gln Pro Pro
                270                 275                 280

GTC TTC AAG GAG AAC GAA GCA CCC ATC AGC GAG GAA ACC TGG AAA AAG               1395
Val Phe Lys Glu Asn Glu Ala Pro Ile Ser Glu Glu Thr Trp Lys Lys
                285                 290                 295

GTT ACA GAC ACC GTC ACT AGT GGA GCT GCC TCT GCC TCT GCT TAT GGA               1443
Val Thr Asp Thr Val Thr Ser Gly Ala Ala Ser Ala Ser Ala Tyr Gly
            300                 305                 310

GCC CTC CTG AGC AGC GTT TTC GTT GCT GTC GGT CTT TTC GCG CTC AGC               1491
Ala Leu Leu Ser Ser Val Phe Val Ala Val Gly Leu Phe Ala Leu Ser
    315                 320                 325

TTC TAAGCGCACA CAGCTCTCCT GCAGCACTTG AGTGGCAGTG CAATGCTTCT                    1544
Phe
330

CTGCCACTCT ATCCACATC GCAGTAATTC AGGCAGCGCA TTAATTCCAT CAAACTCTTT              1604

TCATTGAGAA GAAGCGCTTA ATACTCT                                                 1631
```

( 2 ) INFORMATION FOR SEQ ID NO:6:

( i ) SEQUENCE CHARACTERISTICS:
        ( A ) LENGTH: 330 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Arg | Thr | Ile | Asp | Thr | Met | Thr | Val | Asp | Pro | Thr | Ala | Ala | Arg | Gly |
|---|---|---|---|---|---|---|---|---|---|---|---|---|---|---|---|
| 1 | | | | 5 | | | | | 10 | | | | | 15 | |
| His | Thr | Ile | Ile | Tyr | Ala | Thr | Lys | Glu | Gly | Asp | Thr | Pro | Pro | Thr | Ala |
| | | | 20 | | | | 25 | | | | | 30 | | | |
| Glu | Glu | Ala | Val | Glu | Gln | Trp | Lys | Lys | Gly | Ala | Ala | Arg | Leu | Gly | Thr |
| | | 35 | | | | 40 | | | | | | 45 | | | |
| Gly | Val | Leu | Pro | Ala | Phe | Thr | Lys | Lys | Ser | Lys | Ala | Ala | Asp | Gly | Glu |
| | 50 | | | | | 55 | | | | | 60 | | | | |
| Ile | Tyr | Tyr | Asp | Ser | Ala | Val | Ala | Gly | Phe | Val | Ser | Ile | Met | Thr | Asp |
| 65 | | | | | 70 | | | | | 75 | | | | | 80 |
| Asn | Thr | Arg | Glu | Thr | Ala | Cys | Tyr | Lys | Ala | Thr | Gly | Cys | Thr | Asn | Ala |
| | | | | 85 | | | | | 90 | | | | | 95 | |
| Ala | Leu | Ile | Cys | Leu | Leu | Lys | Gly | Pro | Thr | Leu | Glu | Glu | Asn | Gln | Lys |
| | | | 100 | | | | | 105 | | | | | 110 | | |
| Pro | Ile | Thr | Asp | Glu | Thr | Trp | Lys | Lys | Val | Leu | Asp | Val | Tyr | Gly | Glu |
| | | 115 | | | | | 120 | | | | | 125 | | | |
| Lys | Met | Asp | Phe | Lys | Glu | Arg | Glu | Glu | Gly | Glu | Ser | Cys | Leu | Thr | Glu |
| | 130 | | | | | 135 | | | | | 140 | | | | |
| Ile | Asn | Asp | Phe | Arg | Ala | Gln | Asp | Gly | Leu | Ala | Leu | Pro | Pro | Phe | Ala |
| 145 | | | | | 150 | | | | | 155 | | | | | 160 |
| Ala | Ala | Thr | Asp | Leu | His | Gly | Ala | Lys | Pro | Lys | Ala | Ser | Glu | Leu | Ile |
| | | | | 165 | | | | | 170 | | | | | 175 | |
| Gly | Lys | Gly | Leu | Thr | Cys | Glu | Ala | Leu | Lys | Ser | Gly | Asn | Ala | Pro | Ile |
| | | | 180 | | | | | 185 | | | | | 190 | | |
| Leu | Phe | Thr | Asp | Gln | Glu | Ile | Ser | Leu | Met | Tyr | Tyr | Met | Gly | Glu | Thr |
| | | 195 | | | | | 200 | | | | | 205 | | | |
| Ala | Thr | Cys | Ser | Leu | Ala | Val | Arg | Glu | Trp | Lys | Asn | Gly | Ile | Asp | Leu |
| | 210 | | | | | 215 | | | | | 220 | | | | |
| Phe | Ser | Asp | Phe | Thr | Ile | Pro | Pro | Lys | Tyr | Thr | Ser | Thr | Glu | Glu | Val |
| 225 | | | | | 230 | | | | | 235 | | | | | 240 |
| Tyr | Lys | Lys | Gly | Ala | Ala | Thr | Asn | Phe | Ile | Ser | Leu | Val | Ser | Glu | Gly |
| | | | | 245 | | | | | 250 | | | | | 255 | |
| Thr | Asp | Thr | Lys | Ile | Lys | Cys | Tyr | Thr | Val | Thr | Gly | Cys | Ser | Glu | Pro |
| | | | 260 | | | | | 265 | | | | | 270 | | |
| Gly | Leu | Leu | Cys | Leu | Leu | Gln | Pro | Pro | Val | Phe | Lys | Glu | Asn | Glu | Ala |
| | | 275 | | | | | 280 | | | | | 285 | | | |
| Pro | Ile | Ser | Glu | Glu | Thr | Trp | Lys | Lys | Val | Thr | Asp | Thr | Val | Thr | Ser |
| | 290 | | | | | 295 | | | | | 300 | | | | |
| Gly | Ala | Ala | Ser | Ala | Ser | Ala | Tyr | Gly | Ala | Leu | Leu | Ser | Ser | Val | Phe |
| 305 | | | | | 310 | | | | | 315 | | | | | 320 |
| Val | Ala | Val | Gly | Leu | Phe | Ala | Leu | Ser | Phe | | | | | | |
| | | | | 325 | | | | | 330 | | | | | | |

( 2 ) INFORMATION FOR SEQ ID NO:7:

( i ) SEQUENCE CHARACTERISTICS:
        ( A ) LENGTH: 800 base pairs
        ( B ) TYPE: nucleic acid
        ( C ) STRANDEDNESS: double
        ( D ) TOPOLOGY: linear ( i i ) MOLECULE TYPE: cDNA to mRNA ( v i i ) IMMEDIATE SOURCE:
        ( B ) CLONE: Eam20E ( i x ) FEATURE:

(A) NAME/KEY: CDS
(B) LOCATION: 2..508

(xi) SEQUENCE DESCRIPTION: SEQ ID NO:7:

```
T TTT TGT TTT GCT TTT TCT TGT TTT TTA CTC GGT GTT GGG GCT GGA          46
  Phe Cys Phe Ala Phe Ser Cys Phe Leu Leu Gly Val Gly Ala Gly
  1             5                   10                  15

TGG TCT TCA AGC TTC TGG GTT GTT GTT GCA TGC ATG TGG CTG ATA CTT        94
Trp Ser Ser Ser Phe Trp Val Val Val Ala Cys Met Trp Leu Ile Leu
                20                  25                  30

TTC TTC GGA GGG TCT CTT CTT CCT GCT GCT ACT GGG GTT GTT ATT GCT        142
Phe Phe Gly Gly Ser Leu Leu Pro Ala Ala Thr Gly Val Val Ile Ala
            35                  40                  45

TCT GTT CCT GTT GAA GTT AGA GCA TTC GGC AGC GGT TTT TGT TTA ATG        190
Ser Val Pro Val Glu Val Arg Ala Phe Gly Ser Gly Phe Cys Leu Met
        50                  55                  60

GTT TAT AAT GTC GCT GGC TAT GTC CTC GGT CCC TTC TTA CCT GGC ATA        238
Val Tyr Asn Val Ala Gly Tyr Val Leu Gly Pro Phe Leu Pro Gly Ile
    65                  70                  75

CTC ATA GAA GCA GCA AAC CTT ACC TGG GGA ATG AGA GTG ATT TAC CTT        286
Leu Ile Glu Ala Ala Asn Leu Thr Trp Gly Met Arg Val Ile Tyr Leu
80                  85                  90                  95

TGG TCT ATT AAT GGC GTT CTC GGG TTT GCA TTA GCG TGC TGC TTC CTC        334
Trp Ser Ile Asn Gly Val Leu Gly Phe Ala Leu Ala Cys Cys Phe Leu
                100                 105                 110

TGG CGC TTC AAA ATA CAC CCT GCC TTC ATC TCC GAC GAT GAT GAA GAA        382
Trp Arg Phe Lys Ile His Pro Ala Phe Ile Ser Asp Asp Asp Glu Glu
            115                 120                 125

CCA TGG CAG CAG CAG CAG CAG CAG CAG CAA CAG CAG CAG CAG CAG TTG        430
Pro Trp Gln Gln Gln Gln Gln Gln Gln Gln Gln Gln Gln Gln Gln Leu
        130                 135                 140

CAG CTG CAG CAG CTG CAG TTG GAG ACG AAA AGC GAA CTC AGG GAT AGT        478
Gln Leu Gln Gln Leu Gln Leu Glu Thr Lys Ser Glu Leu Arg Asp Ser
    145                 150                 155

GAT TCT TGT GTC ACA GCA GCG GCT AAT TGATGCGGTT GCAACAAGCA              525
Asp Ser Cys Val Thr Ala Ala Ala Asn
160                 165

GCAAGCCTTC AATGGTAGTT GCTCACTGAT GTATTCCTT CTAGTTGAGT TGTGTGCATG       585

CCAGCATGCA TGCACGAACA ACAGACTAGC AGTGGCTCAT CTGCTGCATG CAGCTGCATG      645

CAACTGCATG CAACTGAAAA GCCCTGCGGA GTTAAGCTGT TTGTCTTTGC TTCTTGTCTT      705

GTGCATCGGT TGGCTGGCAT GCGCTGCTGC ATGCCCAGCG AACCTTTCTT CGAAATATTC      765

TGCGGACACT ATAAACTGAT TTCTCTCCTT CTTTG                                 800
```

(2) INFORMATION FOR SEQ ID NO:8:

(i) SEQUENCE CHARACTERISTICS:
(A) LENGTH: 168 amino acids
(B) TYPE: amino acid
(D) TOPOLOGY: linear (ii) MOLECULE TYPE: protein (xi) SEQUENCE DESCRIPTION: SEQ ID NO:8:

```
Phe Cys Phe Ala Phe Ser Cys Phe Leu Leu Gly Val Gly Ala Gly Trp
1               5                   10                  15

Ser Ser Ser Phe Trp Val Val Val Ala Cys Met Trp Leu Ile Leu Phe
                20                  25                  30

Phe Gly Gly Ser Leu Leu Pro Ala Ala Thr Gly Val Val Ile Ala Ser
            35                  40                  45
```

|     |     |     |     |     |     |     |     |     |     |     |     |     |     |     |
| --- | --- | --- | --- | --- | --- | --- | --- | --- | --- | --- | --- | --- | --- | --- |
| Val | Pro | Val | Glu | Val | Arg | Ala | Phe | Gly | Ser | Gly | Phe | Cys | Leu | Met | Val |
|     | 50  |     |     |     | 55  |     |     |     |     | 60  |     |     |     |     |
| Tyr | Asn | Val | Ala | Gly | Tyr | Val | Leu | Gly | Pro | Phe | Leu | Pro | Gly | Ile | Leu |
| 65  |     |     |     |     | 70  |     |     |     |     | 75  |     |     |     |     | 80  |
| Ile | Glu | Ala | Ala | Asn | Leu | Thr | Trp | Gly | Met | Arg | Val | Ile | Tyr | Leu | Trp |
|     |     |     |     | 85  |     |     |     |     | 90  |     |     |     |     | 95  |     |
| Ser | Ile | Asn | Gly | Val | Leu | Gly | Phe | Ala | Leu | Ala | Cys | Cys | Phe | Leu | Trp |
|     |     |     | 100 |     |     |     |     | 105 |     |     |     |     | 110 |     |     |
| Arg | Phe | Lys | Ile | His | Pro | Ala | Phe | Ile | Ser | Asp | Asp | Glu | Glu | Pro |
|     |     | 115 |     |     |     |     | 120 |     |     |     |     | 125 |     |     |
| Trp | Gln | Gln | Gln | Gln | Gln | Gln | Gln | Gln | Gln | Gln | Gln | Gln | Leu | Gln |
|     | 130 |     |     |     |     | 135 |     |     |     |     | 140 |     |     |     |
| Leu | Gln | Gln | Leu | Gln | Leu | Glu | Thr | Lys | Ser | Glu | Leu | Arg | Asp | Ser | Asp |
| 145 |     |     |     |     | 150 |     |     |     |     | 155 |     |     |     |     | 160 |
| Ser | Cys | Val | Thr | Ala | Ala | Ala | Asn |
|     |     |     |     | 165 |     |     |     |

( 2 ) INFORMATION FOR SEQ ID NO:9:

( i ) SEQUENCE CHARACTERISTICS:
        ( A ) LENGTH: 2375 base pairs
        ( B ) TYPE: nucleic acid
        ( C ) STRANDEDNESS: single
        ( D ) TOPOLOGY: linear ( i i ) MOLECULE TYPE: cDNA to mRNA ( v i i ) IMMEDIATE SOURCE:
        ( B ) CLONE: Eam100E ( i x ) FEATURE:
        ( A ) NAME/KEY: CDS
        ( B ) LOCATION: 3..1859

( x i ) SEQUENCE DESCRIPTION: SEQ ID NO:9:

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| TC  | GGG | GTT | GCT | AAG | AGG | GGA | GAC | GTC | ACA | GCT | TGC | AGG | TAC | TCC | GAC |  47 |
|     | Gly | Val | Ala | Lys | Arg | Gly | Asp | Val | Thr | Ala | Cys | Arg | Tyr | Ser | Asp |     |
|     | 1   |     |     |     | 5   |     |     |     |     | 10  |     |     |     |     | 15  |     |
| TCC | AGC | TGT | TAC | TTG | AGG | AAT | ATC | GAG | TAC | ACT | GGA | GCA | GCC | TAC | AAA |  95 |
| Ser | Ser | Cys | Tyr | Leu | Arg | Asn | Ile | Glu | Tyr | Thr | Gly | Ala | Ala | Tyr | Lys |     |
|     |     |     |     | 20  |     |     |     |     | 25  |     |     |     |     | 30  |     |     |
| GAC | GTC | AAG | AAG | AGC | TAC | TTA | CAA | GAG | TGC | CCG | CAT | TTG | TGC | GCC | CTA | 143 |
| Asp | Val | Lys | Lys | Ser | Tyr | Leu | Gln | Glu | Cys | Pro | His | Leu | Cys | Ala | Leu |     |
|     |     |     | 35  |     |     |     |     | 40  |     |     |     |     | 45  |     |     |     |
| GAA | GCA | CGC | TGT | CAA | CGC | TGG | ACA | TAC | AAC | AAG | ACC | AAG | AAA | TCC | TGC | 191 |
| Glu | Ala | Arg | Cys | Gln | Arg | Trp | Thr | Tyr | Asn | Lys | Thr | Lys | Lys | Ser | Cys |     |
|     |     | 50  |     |     |     |     | 55  |     |     |     |     | 60  |     |     |     |     |
| AGG | CTC | TTC | GAT | TTG | GAA | TCC | TCT | AAG | GCC | GGC | ACC | TAC | ACC | TCA | CAA | 239 |
| Arg | Leu | Phe | Asp | Leu | Glu | Ser | Ser | Lys | Ala | Gly | Thr | Tyr | Thr | Ser | Gln |     |
|     | 65  |     |     |     |     | 70  |     |     |     |     | 75  |     |     |     |     |     |
| CCC | TCG | TGG | AGT | GGC | CCT | AAG | AAC | GGC | TGC | GCT | TCT | GAA | CCC | CTG | TAC | 287 |
| Pro | Ser | Trp | Ser | Gly | Pro | Lys | Asn | Gly | Cys | Ala | Ser | Glu | Pro | Leu | Tyr |     |
| 80  |     |     |     |     | 85  |     |     |     |     | 90  |     |     |     |     | 95  |     |
| AAT | GCA | TTT | CAG | AAT | GTG | CCT | TCA | TGC | AGC | ATG | AGA | GGC | GTG | CGC | TAT | 335 |
| Asn | Ala | Phe | Gln | Asn | Val | Pro | Ser | Cys | Ser | Met | Arg | Gly | Val | Arg | Tyr |     |
|     |     |     |     | 100 |     |     |     |     | 105 |     |     |     |     | 110 |     |     |
| GAC | GGG | GTG | CCT | TTT | GCA | GTT | GAG | AAA | ACC | GAG | ACC | GCA | AAC | GCA | TGC | 383 |
| Asp | Gly | Val | Pro | Phe | Ala | Val | Glu | Lys | Thr | Glu | Thr | Ala | Asn | Ala | Cys |     |
|     |     |     | 115 |     |     |     |     | 120 |     |     |     |     | 125 |     |     |     |
| CAA | GCT | AAA | TGC | CAG | ACG | ACC | ACA | GGA | TGT | GAA | GCC | TTC | TCT | TAC | GAT | 431 |
| Gln | Ala | Lys | Cys | Gln | Thr | Thr | Thr | Gly | Cys | Glu | Ala | Phe | Ser | Tyr | Asp |     |
|     |     | 130 |     |     |     |     | 135 |     |     |     |     | 140 |     |     |     |     |

| | | | | | | | | | | | | | | | | |
|---|---|---|---|---|---|---|---|---|---|---|---|---|---|---|---|---|
| ATG | AAA | GGA | GGA | GTA | TGC | TAC | ATG | CAT | ATT | GCA | TTT | GCA | GTG | ATG | TCG | 479 |
| Met | Lys 145 | Gly | Gly | Val | Cys | Tyr 150 | Met | His | Ile | Ala | Phe 155 | Ala | Val | Met | Ser | |
| AAG | CGC | CCC | AAC | TAC | AAC | TTC | GTC | TCA | GGC | CCG | CGT | CAA | TGC | GCA | GGC | 527 |
| Lys 160 | Arg | Pro | Asn | Tyr | Asn 165 | Phe | Val | Ser | Gly | Pro 170 | Arg | Gln | Cys | Ala | Gly 175 | |
| TGC | ATG | AAG | AAG | GGT | GTA | GAG | TAC | AAC | GGC | GAA | ATC | ATC | AGG | GAG | CTC | 575 |
| Cys | Met | Lys | Lys | Gly 180 | Val | Glu | Tyr | Asn | Gly 185 | Glu | Ile | Ile | Arg | Glu 190 | Leu | |
| ACC | ACG | GCA | GTA | GAG | ACC | GAA | GAA | GAG | TGC | CAG | CTG | CAC | TGC | CAA | GCT | 623 |
| Thr | Thr | Ala | Val 195 | Glu | Thr | Glu | Glu | Glu 200 | Cys | Gln | Leu | His | Cys 205 | Gln | Ala | |
| ATA | TCG | ACC | TGC | GCT | GTA | TTC | TCG | TAC | CGT | GGA | AGC | TTC | TGC | AGA | CTC | 671 |
| Ile | Ser | Thr 210 | Cys | Ala | Val | Phe | Ser 215 | Tyr | Arg | Gly | Ser | Phe 220 | Cys | Arg | Leu | |
| ATT | GGA | AGA | GAT | GCT | ACA | ACC | GAG | CAA | AGC | CCC | CTA | GCA | ACA | AGC | GGC | 719 |
| Ile | Gly | Arg 225 | Asp | Ala | Thr | Thr | Glu 230 | Gln | Ser | Pro | Leu | Ala 235 | Thr | Ser | Gly | |
| ACG | AAG | CAC | TGT | GCA | GGA | GAT | TGC | TAT | CTG | CAA | GGT | GTC | CAT | AGC | CCA | 767 |
| Thr 240 | Lys | His | Cys | Ala | Gly 245 | Asp | Cys | Tyr | Leu | Gln 250 | Gly | Val | His | Ser | Pro 255 | |
| CGG | CGT | GAT | TAC | GGG | TAC | GTG | AAG | GAA | TTG | AGC | GGC | AAG | ACA | GCT | GAA | 815 |
| Arg | Arg | Asp | Tyr | Gly 260 | Tyr | Val | Lys | Glu | Leu 265 | Ser | Gly | Lys | Thr | Ala 270 | Glu | |
| CAG | TGC | CGC | GAC | ACG | TGC | AAA | GCA | GAT | GAG | AAG | TGC | ACG | AGC | TTC | ACA | 863 |
| Gln | Cys | Arg | Asp 275 | Thr | Cys | Lys | Ala | Asp 280 | Glu | Lys | Cys | Thr | Ser 285 | Phe | Thr | |
| CAC | TGG | AAT | GAC | AAA | CGG | TGC | TAC | TTG | AAA | GAT | GAC | GAG | TCC | TTC | AGA | 911 |
| His | Trp | Asn | Asp 290 | Lys | Arg | Cys | Tyr | Leu 295 | Lys | Asp | Asp | Glu | Ser 300 | Phe | Arg | |
| TAT | CTT | TCA | CCT | ATC | GAG | GGG | GCC | GTC | ACA | GGC | TTC | CCA | ACC | TGC | TCT | 959 |
| Tyr | Leu 305 | Ser | Pro | Ile | Glu | Gly 310 | Ala | Val | Thr | Gly | Phe 315 | Pro | Thr | Cys | Ser | |
| ATC | TGC | ATG | AGG | GAA | GGA | GTA | AGG | ATC | CTA | GCA | AAC | GAT | TCG | AAT | CTC | 1007 |
| Ile | Cys | Met | Arg | Glu | Gly 325 | Val | Arg | Ile | Leu | Ala 330 | Asn | Asp | Ser | Asn | Leu 335 | |
| Ile 320 | | | | | | | | | | | | | | | | |
| CTG | TGG | AAC | TTG | GAA | GCC | GGC | AAT | GCA | GAA | GAA | TGT | AAG | ATT | CGC | TGC | 1055 |
| Leu | Trp | Asn | Leu | Glu 340 | Ala | Gly | Asn | Ala | Glu 345 | Glu | Cys | Lys | Ile | Arg 350 | Cys | |
| GGA | CTC | ATG | AGC | TCG | TGC | ACT | CGC | TTT | GCT | TTC | AAT | ATA | GTG | ACA | AAG | 1103 |
| Gly | Leu | Met | Ser 355 | Ser | Cys | Thr | Arg | Phe 360 | Ala | Phe | Asn | Ile | Val 365 | Thr | Lys | |
| CAA | TGC | AGT | CTT | CTC | TCA | GGC | GAA | GGC | GAG | TTG | GTG | GAA | GCA | CGT | GAC | 1151 |
| Gln | Cys | Ser 370 | Leu | Leu | Ser | Gly | Glu 375 | Gly | Glu | Leu | Val | Glu 380 | Ala | Arg | Asp | |
| TAC | GTC | TCC | GGG | CCC | GCT | AAA | TGC | TTA | ACG | GAC | ATC | TCT | TGC | TTC | CAG | 1199 |
| Tyr | Val | Ser 385 | Gly | Pro | Ala | Lys 390 | Cys | Leu | Thr | Asp | Ile 395 | Ser | Cys | Phe | Gln | |
| AGA | GAT | GTC | GCT | TTC | ACT | GGC | GGC | GAG | ACA | GTT | GCT | ACA | GAT | GTG | ACA | 1247 |
| Arg 400 | Asp | Val | Ala | Phe 405 | Thr | Gly | Gly | Glu | Thr 410 | Val | Ala | Thr | Asp | Val 415 | Thr | |
| GAG | AAC | GCA | GGG | CTC | TGC | ATG | CGG | TGG | TGT | GCA | AAG | GAA | GCA | CAA | TGC | 1295 |
| Glu | Asn | Ala | Gly | Leu 420 | Cys | Met | Arg | Trp | Cys 425 | Ala | Lys | Glu | Ala | Gln 430 | Cys | |
| ACG | CAC | TTC | ACC | TTT | ACT | TTT | GCT | GAA | GAT | CGT | CTC | TCC | GGC | CAA | TGC | 1343 |
| Thr | His | Phe | Thr 435 | Phe | Thr | Phe | Ala | Glu 440 | Asp | Arg | Leu | Ser | Gly 445 | Gln | Cys | |
| ACT | CTT | CTT | AAG | GGG | GAT | CTG | AAT | GTA | ACG | AAA | ACT | AAG | GGT | GCT | GTC | 1391 |
| Thr | Leu | Leu | Lys 450 | Gly | Asp | Leu | Asn | Val 455 | Thr | Lys | Thr | Lys | Gly 460 | Ala | Val | |

```
TCA GGC CCA AAG CGG TGT TTC GAA CTG CTC TCT CTC TGC GAG GAA CCA      1439
Ser Gly Pro Lys Arg Cys Phe Glu Leu Leu Ser Leu Cys Glu Glu Pro
    465             470                 475

GAT GTA GAG TAT GTC GGA GGT GAG ATC TCC AAC GTG GAT GCA GAA GAT      1487
Asp Val Glu Tyr Val Gly Gly Glu Ile Ser Asn Val Asp Ala Glu Asp
480                     485                 490                 495

ACA ACA CAG TGC AGA GAG CTC TGC TAC AAA CAC CCG ATG TGC CGG CTC      1535
Thr Thr Gln Cys Arg Glu Leu Cys Tyr Lys His Pro Met Cys Arg Leu
                500                 505                 510

TAT ACA TTC ACC CCA GCG GAG AAG AAG TGC TCA CTG AAG AAG ATT GAA      1583
Tyr Thr Phe Thr Pro Ala Glu Lys Lys Cys Ser Leu Lys Lys Ile Glu
            515                 520                 525

GCT GTT GCA GGA CGT ACA ACG AAA AAA CAA GGC AAA GTA TCT GGA TCT      1631
Ala Val Ala Gly Arg Thr Thr Lys Lys Gln Gly Lys Val Ser Gly Ser
                530                 535                 540

AAG GTA GGG TGC GCT CGT AGT GCT AGA GGT GGC TAT GCT TAT AAA GGA      1679
Lys Val Gly Cys Ala Arg Ser Ala Arg Gly Gly Tyr Ala Tyr Lys Gly
    545                 550                 555

ACC TCC TTC AAG ACT ATT CCG GGC TTA CCT CAT GAG ACA GCC TGC CGG      1727
Thr Ser Phe Lys Thr Ile Pro Gly Leu Pro His Glu Thr Ala Cys Arg
560                 565                 570                 575

CTG CAA TGC GAA TAC GAG AGC AAC TGC ATT GCT TTC ACC TTC GAC ACC      1775
Leu Gln Cys Glu Tyr Glu Ser Asn Cys Ile Ala Phe Thr Phe Asp Thr
                580                 585                 590

GAG AAG AAG GTG TGC TCT CTT AAG GCC CGC GTG GAC TTA GTA GAA CCC      1823
Glu Lys Lys Val Cys Ser Leu Lys Ala Arg Val Asp Leu Val Glu Pro
            595                 600                 605

AGA GAT ACA GGT GTT ATT GGG CCT AAA CGC GAA TAAACAGCTG CTAATAATGT    1876
Arg Asp Thr Gly Val Ile Gly Pro Lys Arg Glu
        610                 615

AATTGAAGCT GTTGCTTCTT CTGCTGGAGC TTGTGCTTGT CGCTCGCTGC ACGAGAACAC   1936

TGGCAGGCAT CGATTCGCAG CTGTATCTCG GTCGGCTTCA TGGTTACTTC CATGTTAGCG   1996

ACTGCACTGC ATTGCTTTCT TCTTTTCTCT TCTCTATTCC CCTCACTTCT TAGCCTGCAT   2056

CCCAAAGGGT TCAGGCATTC AAGAGAAGAG GGTGCTCTCT TCTTTCTCAC GGTGCAGATA   2116

CACGAGACGT AAATAAACAC AATTAACAAA ACACACCCAC AGCGAGGACA GAACATCATC   2176

AGCATTTATA TCACTGCGTT GCATGCATTT AATAACGGCA AGAACGACAG GGGAGCGAGC   2236

GACACAGCAG TCTAGACGTC GCTCTGTGCT CCCTTGCAAG ATGTCTTTTC GCATACATCA   2296

AACAGAAGAA AAGAAAGACG TGCAGTTTGA ACTGACGTTT GTTCATGCAT GCATGCATGC   2356

AAAAAAAAAA AGGCACGAG                                                2375
```

( 2 ) INFORMATION FOR SEQ ID NO:10:

( i ) SEQUENCE CHARACTERISTICS:
        ( A ) LENGTH: 618 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Gly Val Ala Lys Arg Gly Asp Val Thr Ala Cys Arg Tyr Ser Asp Ser
 1               5                  10                  15

Ser Cys Tyr Leu Arg Asn Ile Glu Tyr Thr Gly Ala Ala Tyr Lys Asp
                20                  25                  30

Val Lys Lys Ser Tyr Leu Gln Glu Cys Pro His Leu Cys Ala Leu Glu
            35                  40                  45

Ala Arg Cys Gln Arg Trp Thr Tyr Asn Lys Thr Lys Lys Ser Cys Arg
```

-continued

| | | 50 | | | | 55 | | | | | 60 | | | |
|---|---|---|---|---|---|---|---|---|---|---|---|---|---|---|
| Leu | Phe | Asp | Leu | Glu | Ser | Ser | Lys | Ala | Gly | Thr | Tyr | Thr | Ser | Gln | Pro |
| 65 | | | | | 70 | | | | 75 | | | | | 80 |
| Ser | Trp | Ser | Gly | Pro | Lys | Asn | Gly | Cys | Ala | Ser | Glu | Pro | Leu | Tyr | Asn |
| | | | | 85 | | | | 90 | | | | | 95 | |
| Ala | Phe | Gln | Asn | Val | Pro | Ser | Cys | Ser | Met | Arg | Gly | Val | Arg | Tyr | Asp |
| | | | 100 | | | | 105 | | | | | 110 | | |
| Gly | Val | Pro | Phe | Ala | Val | Glu | Lys | Thr | Glu | Thr | Ala | Asn | Ala | Cys | Gln |
| | | 115 | | | | 120 | | | | | 125 | | | |
| Ala | Lys | Cys | Gln | Thr | Thr | Thr | Gly | Cys | Glu | Ala | Phe | Ser | Tyr | Asp | Met |
| | 130 | | | | 135 | | | | 140 | | | | | |
| Lys | Gly | Gly | Val | Cys | Tyr | Met | His | Ile | Ala | Phe | Ala | Val | Met | Ser | Lys |
| 145 | | | | 150 | | | | 155 | | | | | | 160 |
| Arg | Pro | Asn | Tyr | Asn | Phe | Val | Ser | Gly | Pro | Arg | Gln | Cys | Ala | Gly | Cys |
| | | | 165 | | | | 170 | | | | | | 175 | |
| Met | Lys | Lys | Gly | Val | Glu | Tyr | Asn | Gly | Glu | Ile | Ile | Arg | Glu | Leu | Thr |
| | | 180 | | | | 185 | | | | | 190 | | | |
| Thr | Ala | Val | Glu | Thr | Glu | Glu | Cys | Gln | Leu | His | Cys | Gln | Ala | Ile |
| | 195 | | | | 200 | | | | 205 | | | | | |
| Ser | Thr | Cys | Ala | Val | Phe | Ser | Tyr | Arg | Gly | Ser | Phe | Cys | Arg | Leu | Ile |
| | 210 | | | | 215 | | | | 220 | | | | | |
| Gly | Arg | Asp | Ala | Thr | Thr | Glu | Gln | Ser | Pro | Leu | Ala | Thr | Ser | Gly | Thr |
| 225 | | | | 230 | | | | 235 | | | | | | 240 |
| Lys | His | Cys | Ala | Gly | Asp | Cys | Tyr | Leu | Gln | Gly | Val | His | Ser | Pro | Arg |
| | | | 245 | | | | 250 | | | | | 255 | | |
| Arg | Asp | Tyr | Gly | Tyr | Val | Lys | Glu | Leu | Ser | Gly | Lys | Thr | Ala | Glu | Gln |
| | | 260 | | | | 265 | | | | | 270 | | | |
| Cys | Arg | Asp | Thr | Cys | Lys | Ala | Asp | Glu | Lys | Cys | Thr | Ser | Phe | Thr | His |
| | 275 | | | | 280 | | | | 285 | | | | | |
| Trp | Asn | Asp | Lys | Arg | Cys | Tyr | Leu | Lys | Asp | Asp | Glu | Ser | Phe | Arg | Tyr |
| 290 | | | | 295 | | | | 300 | | | | | | |
| Leu | Ser | Pro | Ile | Glu | Gly | Ala | Val | Thr | Gly | Phe | Pro | Thr | Cys | Ser | Ile |
| 305 | | | | 310 | | | | 315 | | | | | | 320 |
| Cys | Met | Arg | Glu | Gly | Val | Arg | Ile | Leu | Ala | Asn | Asp | Ser | Asn | Leu | Leu |
| | | | 325 | | | | 330 | | | | | 335 | | |
| Trp | Asn | Leu | Glu | Ala | Gly | Asn | Ala | Glu | Glu | Cys | Lys | Ile | Arg | Cys | Gly |
| | | 340 | | | | 345 | | | | | 350 | | | |
| Leu | Met | Ser | Ser | Cys | Thr | Arg | Phe | Ala | Phe | Asn | Ile | Val | Thr | Lys | Gln |
| | | 355 | | | | 360 | | | | | 365 | | | |
| Cys | Ser | Leu | Leu | Ser | Gly | Glu | Gly | Glu | Leu | Val | Glu | Ala | Arg | Asp | Tyr |
| | 370 | | | | 375 | | | | | 380 | | | | |
| Val | Ser | Gly | Pro | Ala | Lys | Cys | Leu | Thr | Asp | Ile | Ser | Cys | Phe | Gln | Arg |
| 385 | | | | 390 | | | | 395 | | | | | | 400 |
| Asp | Val | Ala | Phe | Thr | Gly | Gly | Glu | Thr | Val | Ala | Thr | Asp | Val | Thr | Glu |
| | | | 405 | | | | 410 | | | | | 415 | | |
| Asn | Ala | Gly | Leu | Cys | Met | Arg | Trp | Cys | Ala | Lys | Glu | Ala | Gln | Cys | Thr |
| | | | 420 | | | | 425 | | | | | 430 | | |
| His | Phe | Thr | Phe | Thr | Phe | Ala | Glu | Asp | Arg | Leu | Ser | Gly | Gln | Cys | Thr |
| | | 435 | | | | 440 | | | | | 445 | | | |
| Leu | Leu | Lys | Gly | Asp | Leu | Asn | Val | Thr | Lys | Thr | Lys | Gly | Ala | Val | Ser |
| | 450 | | | | 455 | | | | | 460 | | | | |
| Gly | Pro | Lys | Arg | Cys | Phe | Glu | Leu | Leu | Ser | Leu | Cys | Glu | Glu | Pro | Asp |
| 465 | | | | 470 | | | | 475 | | | | | | 480 |

-continued

| Val | Glu | Tyr | Val | Gly 485 | Gly | Glu | Ile | Ser | Asn 490 | Val | Asp | Ala | Glu | Asp 495 | Thr |
| --- | --- | --- | --- | --- | --- | --- | --- | --- | --- | --- | --- | --- | --- | --- | --- |
| Thr | Gln | Cys | Arg 500 | Glu | Leu | Cys | Tyr | Lys 505 | His | Pro | Met | Cys | Arg 510 | Leu | Tyr |
| Thr | Phe | Thr 515 | Pro | Ala | Glu | Lys | Lys 520 | Cys | Ser | Leu | Lys | Lys 525 | Ile | Glu | Ala |
| Val | Ala 530 | Gly | Arg | Thr | Thr | Lys 535 | Lys | Gln | Gly | Lys | Val 540 | Ser | Gly | Ser | Lys |
| Val 545 | Gly | Cys | Ala | Arg | Ser 550 | Ala | Arg | Gly | Gly | Tyr 555 | Ala | Tyr | Lys | Gly | Thr 560 |
| Ser | Phe | Lys | Thr | Ile 565 | Pro | Gly | Leu | Pro | His 570 | Glu | Thr | Ala | Cys | Arg 575 | Leu |
| Gln | Cys | Glu | Tyr 580 | Glu | Ser | Asn | Cys | Ile 585 | Ala | Phe | Thr | Phe | Asp 590 | Thr | Glu |
| Lys | Lys | Val 595 | Cys | Ser | Leu | Lys | Ala 600 | Arg | Val | Asp | Leu | Val 605 | Glu | Pro | Arg |
| Asp | Thr 610 | Gly | Val | Ile | Gly | Pro 615 | Lys | Arg | Glu | | | | | | |